(12) United States Patent
Kuhnt et al.

(10) Patent No.: US 6,194,464 B1
(45) Date of Patent: Feb. 27, 2001

(54) IMIDIC ACID DERIVATIVES AND THEIR USE AS PESTICIDES

(75) Inventors: Dietmar Kuhnt, Burscheid; Ulrich Heinemann, Leichlingen; Herbert Gayer, Monheim; Peter Gerdes, Aachen; Jörg Stetter, Wuppertal; Ralf Tiemann, Leverkusen; Klaus Stenzel, Düsseldorf; Stefan Dutzmann, Hilden, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/300,911

(22) Filed: Apr. 28, 1999

Related U.S. Application Data

(62) Division of application No. 08/793,709, filed as application No. PCT/EP95/03391 on Aug. 28, 1995, now abandoned.

(30) Foreign Application Priority Data

Sep. 9, 1994 (DE) ................................. 44 32 088
Mar. 10, 1995 (DE) ............................... 195 08 573

(51) Int. Cl.$^7$ .......................... A01N 37/34; C07C 255/62; C07C 261/04
(52) U.S. Cl. .......................... 514/609; 514/523; 558/409; 564/103; 564/105
(58) Field of Search .............................. 558/409; 564/103, 564/105; 514/523, 609

(56) References Cited

U.S. PATENT DOCUMENTS 5,360,810 * 11/1994 Hayase et al. ....................... 514/346

FOREIGN PATENT DOCUMENTS

| 463488 | 1/1992 | (EP) . |
| 564928 | 10/1993 | (EP) . |
| 644183 | 3/1995 | (EP) . |
| 656352 | 6/1995 | (EP) . |
| 9422844 | 10/1994 | (WO) . |
| 9426700 | 11/1994 | (WO) . |

* cited by examiner

*Primary Examiner*—Shailendra Kumar
(74) *Attorney, Agent, or Firm*—Norris McLaughlin & Marcus P.A.

(57) ABSTRACT

The present invention relates to new imidic acid derivatives of the formula (I)

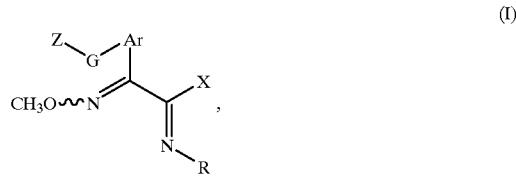

to a plurality of processes for their preparation, and to their use as pesticides.

8 Claims, No Drawings

IMIDIC ACID DERIVATIVES AND THEIR USE AS PESTICIDES

This application is a division of U.S. Ser. No. 08/793,709, Filed Mar. 4, 1997, now abandoned, which, in turn, is a 371 of PCT/EP95/03391, filed Aug. 28, 1995.

The present invention relates to new imidic acid derivatives, to a plurality of processes for their preparation, and to their use as pesticides.

It is known that various substituted alkoximino- and alkoxymethyleneacetamides have fungicidal properties (cf., for example, EP-A 398 692, EP-A 468 775, DE-A 40 30 038 and WO-A 92/13 830).

However, the efficacy of these prior-art compounds is not entirely satisfactory in all fields of application, in particular when low application rates and concentrations are used.

New imidic acid derivatives have been found of the general formula (I)

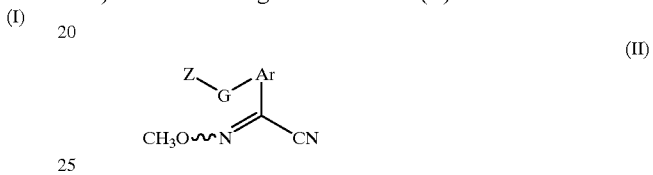

(I)

in which

R represents hydrogen, cyano or the groups —CO—R$^1$, —CS—R$^2$ and —S(O)$_m$—R$^3$, where R$^1$, R$^2$ and R$^3$ in each case represent alkyl, alkoxy, alkylthio, amino, alkylamino or dialkylamino and m represents the numbers 0, 1 or 2;

X represents alkoxy, alkylthio, amino, alkylamino or dialkylamino, or

X and R together with the carbon or nitrogen atom to which they are bonded represent a triazole radical of the formula

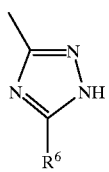

where

R$^6$ represents alkyl, hydroxyl, mercapto, amino, alkylamino or dialkylamino;

Ar represents in each case optionally substituted arylene or heteroarylene;

G represents a single bond, represents oxygen, or represents in each case optionally halogen-, hydroxyl-, alkyl-, halogenoalkyl- or cycloalkyl-substituted alkanediyl, alkenediyl, oxaalkenediyl, alkinediyl or one of the following groups:
-Q—CQ-, —CQ-Q-, —CH$_2$—Q-; -Q—CH$_2$—, —CQ-Q—CH$_2$—, —CH$_2$—Q—CQ-, -Q—CQ—CH$_2$—, -Q—CQ-Q—CH$_2$—, —N=N—, —S(O)$_n$—, —CH$_2$—S(O)$_n$—, —CQ-, —S(O)$_n$—CH$_2$—, —C(R$^4$)=N—O—, —C(R$^4$)=N—O—CH$_2$—, -Q—C(R$^4$)=N—O—CH$_2$—, —NH—C(R$^4$)=N—O—CH$_2$—, —N(R$^5$)-, —CQ-N(R$^5$)-, —N(R$^5$)—CQ-, -Q—CQ—N(R$^5$)-, —N=C(R$^4$)-Q—CH$_2$—, —CH$_2$—O—N=C(R$^4$)-, —N(R$^5$)—CQ-Q-, —CQ—N(R$^5$)—CQ-Q-, —N(R$^5$)—CQ-Q—CH$_2$—, —CQ—CH$_2$— or —N=N—C(R$^4$)=N—O—, where Q represents oxygen or sulphur, n represents the numbers 0, 1 or 2, R$^4$ represents hydrogen, cyano or in each case optionally substituted alkyl, alkoxy, alkylthio, alkylamino, dialkylamino or cycloalkyl, and R$^5$ represents hydrogen, hydroxyl, cyano or in each case optionally substituted alkyl, alkoxy or cycloalkyl; and Z represents in each case optionally substituted alkyl, alkenyl, alkinyl, cycloalkyl, aryl or heterocyclyl, with the exception of those compounds in which simultaneously R represents hydrogen, G represents oxygen or the group —OCH$_2$— and Z represents in each case optionally substituted aryl or 2-pyridyl.

Furthermore, it has been found that the new imidic acid derivatives of the general formula (I) are obtained when a) nitrites of the general formula (II)

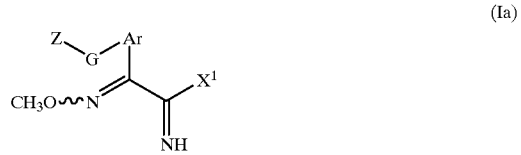

(II)

in which

Ar, G and Z have the abovementioned meanings are reacted with (thio)alcohols of the general formula (III)

H—X$^1$  (III)

in which

X$^1$ represents alkoxy or alkylthio, or with their alkali metal salts, if appropriate in the presence of a diluent and if appropriate in the presence of a reaction auxiliary;

or b) the imidates which can be obtained by process (a) which have the general formula (Ia)

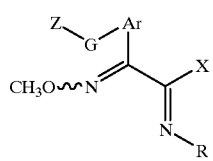

(Ia)

in which

Ar, G, Z and X$^1$ have the abovementioned meanings, are reacted with reactive acid derivatives, in particular with acid halides of the general formula (IV)

Hal-R  (IV)

in which

R has the abovementioned meaning and

Hal represents halogen, or with the corresponding anhydrides, if appropriate in the presence of a diluent and if appropriate in the presence of a reaction auxiliary;

or c) the imidates which can be obtained by process (a) which have the general formula (Ia)

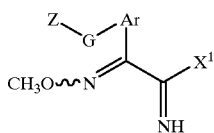

(Ia)

in which

Ar, G, Z and $X^1$ have the abovementioned meanings, are reacted with cyanamide, of the formula (V), $$NH_2—CN \qquad (V)$$

if appropriate in the presence of a diluent and if appropriate in the presence of a reaction auxiliary;

or d) the imidic acid derivatives which can be obtained by processes (b) and (c) which have the general formula (Ib)

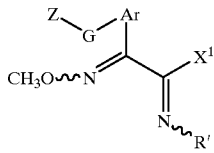

(Ib)

in which

Ar, G, Z and $X^1$ have the abovementioned meanings and

R' represents cyano or the groups —$COR^1$, —$CSR^2$ and —$S(O)_mR^3$, where $R^1$, $R^2$, $R^3$ and m have the abovementioned meanings, are reacted with amines of the general formula (VI)

$$H—X^2 \qquad (VI)$$

in which $X^2$ represents amino, alkylamino or dialkylamino, if appropriate in the presence of a diluent;

or e) the imidic acid derivatives which can be obtained by processes (b) and (c) which have the general formula (Ic)

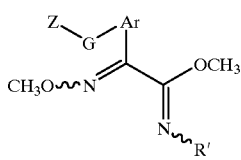

(Ic)

in which

Ar, G, Z and R' have the abovementioned meanings, are reacted with hydrazine or hydrazine hydrate, if appropriate in the presence of a diluent;

or f) the imidates which can be obtained by process (a) which have the general formula (Ia)

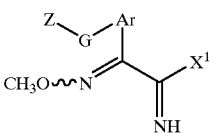

(Ia)

in which

Ar, G, Z and $X^1$ have the abovementioned meanings, are reacted with amines of the general formula (VI)

$$H—X^2 \qquad (VI)$$

in which $X^2$ has the abovementioned meaning, if appropriate in the presence of a diluent.

Finally, it has been found that the new imidic acid derivatives of the general formula (I) exhibit a powerful fungicidal activity.

If appropriate, the compounds according to the invention can exist in the form of mixtures of various isomeric forms which are possible, in particular E and Z isomers. The invention claims not only the E and Z isomers, but also any mixtures of these isomers.

The invention preferably relates to compounds of the formula (I) in which

R represents hydrogen, cyano or the groups —CO—$R^1$, —CS—$R^2$ and —$S(O)_m$—$R^3$, where $R^1$, $R^2$ and $R^3$ represent in each case straight-chain or branched alkyl, alkoxy or alkylthio, each of which has 1 to 4 carbon atoms; amino or in each case straight-chain or branched alkylamino and dialkylamino, each of which has 1 to 4 carbon atoms in the individual alkyl moieties, and m represents the numbers 0, 1 or 2, X represents in each case straight-chain or branched alkoxy or alkylthio, each of which has 1 to 4 carbon atoms; amino or in each case straight-chain or branched alkylamino and dialkylamino, each of which has 1 to 4 carbon atoms in the individual alkyl moieties, X and R together with the carbon or nitrogen atom to which they are bonded represent a triazole radical of the formula

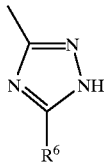

where $R^6$ represents straight-chain or branched alkyl having 1 to 4 carbon atoms, hydroxyl, mercapto, amino or in each case straight-chain or branched alkylamino and dialylano, each of which has 1 to 4 carbon atoms in the individual alkyl moieties, Ar represents in each case optionally substituted phenylene or naphthylene, or represents heteroarylene having 5 or 6 ring members of which at least one represents oxygen, sulphur or nitrogen and, if appropriate, one or two further ring members represent nitrogen, the substituents which are possible preferably being selected from the following enumeration:

halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl, alkenyloxy or alkinyloxy, each of which has 2 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkyl-sulphonyloxy, hydroximinoalkyl or alkoximinoalkyl, each of which has 1 to 6 carbon atoms in the individual alkyl moieties, and in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, G represents a single bond, represents oxygen, or represents in each case optionally halogen-, hydroxyl-, $C_1$–$C_4$-alkyl-, $C_1$–$C_4$-halogenoalkyl- or $C_3$–$C_6$-cycloalkyl-substituted alkanediyl, alkenediyl, oxaalkenediyl or alkinediyl, each of which has up to 4 carbon atoms, or one of the groups which follow:
-Q—CQ-, —CQ-Q-, —CH$_2$—Q-; -Q—CH$_2$—, —CQ-Q—CH$_2$—, —CH$_2$—Q—CQ-, -Q—CQ—CH$_2$—, -Q—CQ-Q—CH$_2$—, —N═N—, —S(O)$_n$—, —CH$_2$—S(O)$_n$—, —CQ-, —S(O)$_n$—CH$_2$—, —C(R$^4$)═N—O—, —C(R$^4$)═N—O—CH$_2$—, -Q—C(R$^4$)═N—O—CH$_2$—, —NH—C(R$^4$)═N—O—CH$_2$—, —N(R$^5$)-, —CQ—N(R$^5$)-, —NR$^5$)—CQ-, -Q—CQ—N(R$^5$)-, —N═C(R$^4$)-Q—CH$_2$—, —CH$_2$—O—N═C(R$^4$)-, —N(R$^5$)—CQ-Q-, —CQ—N($^5$)—CQ-Q-, —N($^5$)—CQ-Q—CH$_2$—, —CQ—CH$_2$— or —N═N—C(R$^4$)═N—, where n represents the numbers 0, 1 or 2, Q represents oxygen or sulphur, R$^4$ represents hydrogen, cyano, or represents alkyl, alkoxy, alkylthio, alkylamino or dialkylamino, each of which has 1 to 6 carbon atoms in the alkyl groups and is optionally substituted by halogen, cyano or $C_1$–$C_4$-alkoxy, or represents cycloalkyl having 3 to 6 carbon atoms which is optionally substituted by halogen, cyano, carboxyl, $C_1$–$C_4$-alkyl or $C_1$–$C_4$-alkoxycarbonyl, and R$^5$ represents hydrogen, hydroxyl, cyano, or represents alkyl having 1 to 6 carbon atoms which is optionally substituted by halogen, cyano or $C_1$–$C_4$-alkoxy, or represents cycloalkyl having 3 to 6 carbon atoms which is optionally substituted by halogen, cyano, carboxyl, $C_1$–$C_4$-alkyl or $C_1$–$C_4$-alkoxycarbonyl, Z represents alkyl having 1 to 8 carbon atoms which is optionally substituted by halogen, cyano, hydroxyl, amino, $C_1$–$C_4$-alkoxy, $C_1$–$C_4$-alkylthio, $C_1$–$C_4$-alkylsulphinyl or $C_1$–$C_4$-alkylsulphonyl (which are in each case optionally substituted by halogen), or represents alkenyl or alkinyl, each of which has up to 8 carbon atoms and is optionally substituted by halogen, or represents cycloalkyl having 3 to 6 carbon atoms which is optionally substituted by halogen, cyano, carboxyl, phenyl (which is optionally substituted by halogen, cyano, $C_1$–$C_4$-allyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl, or represents in each case optionally substituted phenyl, naphthyl or (optionally benzofused) heterocyclyl having 5 or 6 ring members of which at least one represents oxygen, sulphur or nitrogen and optionally one or two further ring members represent nitrogen, the substituents which are possible preferably being selected from the enumeration which follows:

oxygen (as a replacement for two geminal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl moieties, in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, or cycloalkyl having 3 to 6 carbon atoms, heterocyclyl or heterocyclyl-methyl, each of which has 3 to 7 ring members of which in each case 1 to 3 are identical or different hetero atoms—in particular nitrogen, oxygen and/or sulphur—, or phenyl, phenoxy, benzyl, benzyloxy, phenylethyl or phenylethyloxy, each of which is optionally monosubstituted or polysubstituted in the phenyl moiety by identical or different substituents from the series consisting of halogen, cyano, nitro, carboxyl, carbamoyl and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkoxy having 1 to 4 carbon atoms and 1 to 9 identical or different halogen atoms and/or alkylcarbonyl or alkoxycarbonyl, each of which has up to 5 carbon atoms;

with the exception of the compounds excluded above by disclaimer.

In the definitions, the saturated or unsaturated hydrocarbon chains, such as alkyl, alkanediyl, alkenyl or alkinyl, also in combination with hetero atoms, such as in alkoxy, alkylthio or alkylamino, are in each case straight-chain or branched.

Halogen generally represents fluorine, chlorine, bromine or iodine, preferably fluorine, chlorine or bromine, in particular fluorine or chlorine.

The invention particularly relates to compounds of the formula (I) in which

R represents hydrogen, cyano or the groups —CO—R$^1$, —CS—R$^2$ and —S(O)$_m$—R$^3$,
where
   R$^1$ represents methyl, ethyl, n- or i-propyl, n-, i-, s- or t-butyl; methoxy, ethoxy, n- or i-propoxy, n-, i-, s- or t-butoxy; methylthio, ethylthio, n- or i-propylthio, n-, i-, s- or t-butylthio; amino, methylamino, ethylamino, n- or i-propylamino; dimethylamino, methyl-ethyl-amino, diethylamino, methyl-n- or i-propylamino and ethyl-n- or i-propylamino;
   R$^2$ represents methyl, ethyl, n- or i-propyl, n-, i-, s- or t-butyl; methoxy, ethoxy, n- or i-propoxy, n-, i-, s- or t-butoxy; methylthio, ethylthio, n- or i-propylthio, n-, i-, s- or t-butylthio; amino, methylamino, ethylamino, n- or i-propylamino; dimethylamino, methyl-ethyl-amino, diethylamino, methyl-n- or i-propylamino and ethyl-n- or i-propylamino;
   R$^3$ represents methyl, ethyl, n- or i-propyl, n-, i-, s- or t-butyl;
   methoxy, ethoxy, n- or i-propoxy, n-, i-, s- or t-butoxy; methylthio, ethylthio, n- or i-propylthio, n-, i-, s- or t-butylthio; amino, methylamino, ethylamino, n- or i-propylamino; dimethylamino, methyl-ethyl-amino, diethylamino, methyl-n- or i-propylamino and ethyl-n- or i-propylamino; and
   m represents the numbers 0, 1 or 2;
X represents methoxy, ethoxy, n- or i-propoxy, n-, i-, s- or t-butoxy; methylthio, ethylthio, n- or i-propylthio, n-, i-, s- or t-butylthio; amino, methylamino, ethylamino, n- or i-propylamino; dimethylamino, methyl-ethyl-amino, diethylamino, methyl-n- or i-propylamino and ethyl-n- or i-propylamino;
X and R together with the carbon or nitrogen atom to which they are bonded represent a triazole radical of the formula

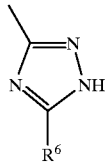

where
   R$^6$ represents methyl, ethyl, n- or i-propyl, n-, i-, s- or t-butyl; hydroxyl; mercapto; amino, methylamino, ethylamino, n- or i-propylamino; dimethyl amino, methyl-ethyl-amino, diethyl amino, methyl-n- or i-propylamino and ethyl-n- or i-propylamino;
Ar represents in each case optionally substituted ortho-, meta- or para-phenylene, or represents furanediyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl, pyrimidinediyl, pyridazinediyl, pyrazinediyl, 1,3,4-triazinediyl or 1,2,3-triazinediyl, the substituents which are possible being selected in particular amongst those of the enumeration which follows:
   fluorine, chlorine, cyano, methyl, ethyl, trifluoromethyl, methoxy, ethoxy, methylthio, methylsulphinyl or methylsulphonyl;
G represents a single bond, represents oxygen or represents in each case optionally fluorine-, chlorine-, hydroxyl-, methyl-, ethyl-, n- or i-propyl-, trifluoromethyl-, cyclopropyl-, cyclobutyl-, cyclopentyl- or cyclohexyl-substituted methylene, dimethylene (ethane-1,2-diyl), ethene-1,2-diyl, ethine-1,2-diyl or one of the groups which follow -Q—CQ-, —CQ-Q-, —CH$_2$—Q—; -Q—CH$_2$—, —CQ-Q—CH$_2$—, —CH$_2$—Q—CQ-, -Q—CQ—CH$_2$—, -Q—CQ-Q—CH$_2$—, —N=N—, —S(O)$_n$—, —CH$_2$—S(O)$_n$—, —CQ-, —S(O)$_n$—CH$_2$—, —C(R$^4$)=N—O—, —C(R$^4$)=N—O—CH$_2$—, -Q—C(R$^4$)=N—O—CH$_2$—, —NH—C(R$^4$)=N—O—CH$_2$—, —N(R$^5$)-, —CQ—N(R$^5$)-, —N($^5$)—CQ-, -Q—CQ—N(R$^5$)-, —N=C(R$^4$)-Q—CH$_2$—, —CH$_2$—O—N=C(R$^4$)-, —N(R$^5$)—CQ-Q-, —CQ—N(R$^5$)—CQ-Q- or —N(R$^5$)—CQ-Q—CH$_2$—,
where
   n represents the numbers 0, 1 or 2,
   Q represents oxygen or sulphur,
   R$^4$ represents hydrogen, cyano, or represents methyl, ethyl, n- or i-propyl, n-, i- or s-butyl, methoxy, ethoxy, propoxy, butoxy, methylthio, ethylthio, propylthio, butylthio, methylamino, ethylamino, propylamino, dimethylamino or diethylamino, which is optionally substituted by fluorine, chlorine, cyano, methoxy or ethoxy, or represents cyclopropyl, cyclobutyl, cyclopentyl or cyclohexyl, each of which is optionally substituted by fluorine, chlorine, cyano, carboxyl, methyl, ethyl, n- or i-propyl, methoxycarbonyl or ethoxycarbonyl, and
   R$^5$ represents hydrogen, hydroxyl, cyano, or represents methyl, ethyl, n- or i-propyl or n-, i-, s- or t-butyl, each of which is optionally substituted by fluorine, chlorine, cyano, methoxy or ethoxy, or represents cyclopropyl, cyclobutyl, cyclopentyl or cyclohexyl, each of which is optionally substituted by fluorine, chlorine, cyano, carboxyl, methyl, ethyl, n- or i-propyl, methoxycarbonyl or ethoxycarbonyl;
Z represents methyl, ethyl, n- or i-propyl or n-, i-, s- or t-butyl, which is optionally substituted by fluorine, chlorine, bromine, cyano, hydroxyl, amino, methoxy, ethoxy, methylthio, ethylthio, methylsulphinyl, ethylsulphinyl, methylsulphonyl or ethylsulphonyl (which are in each case optionally substituted by fluorine and/or chlorine), or represents allyl, crotonyl, 1-methyl-allyl, propargyl or 1-methyl-propargyl, each of which is optionally substituted by fluorine, chlorine or bromine, or represents cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxycarbonyl or ethoxycarbonyl, or represents in each case optionally substituted phenyl, naphthyl, furyl, tetrahydrofuryl, benzofuryl, tetrahydropyranyl, thienyl, benzothienyl, pyrrolyl, dihydropyrrolyl, tetrahydropyrrolyl, benzopyrrolyl, benzodihydropyrrolyl, oxazolyl, benzoxazolyl, isoxazolyl, thiazolyl, benzothiazolyl, isothiazolyl, imidazolyl, benzimidazolyl, oxadiazolyl, thiadiazolyl, pyridinyl, pyrimidinyl, pyridazinyl, pyrazinyl, 1,2,3-triazinyl, 1,2,4-triazinyl or 1,3,5-triazinyl, the substituents which are possible preferably being selected from the enumeration which follows:
   oxygen (as a replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, tri-fluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl; trimethylene (propane-1,3-diyl), methylenedioxy or ethylenedioxy, cyclopropyl, cyclobutyl, cyclopentyl or cyclohexyl, each of which is optionally monosubstituted or polysubstituted by identical or different substituents from the series consisting of fluorine, chlorine, methyl, ethyl or n- or i-propyl, and phenyl, phenoxy, benzyl or benzyloxy, each of which is optionally monosubstituted or polysubstituted in the phenyl moiety by identical or different substituents from the series consisting of fluorine, chlorine, bromine, cyano, nitro, carboxyl, carbamoyl, methyl, ethyl, n- or i-propyl, n-, i-, s- or t-butyl, trifluoromethyl, methoxy, ethoxy, n- or i-propoxy, difluoromethoxy, trifluoromethoxy, acetyl, methoxycarbonyl or ethoxycarbonyl;

with the exception of the compounds excluded above by disclaimer.

A particularly preferred group of compounds according to the invention are those compounds of the formula (I) in which R represents hydrogen, cyano or the groups —CO—R$^1$, —CS—R$^2$ and —S(O)$_m$—R$^3$, where R$^1$ represents methyl, ethyl, methoxy, ethoxy, methylthio, ethylthio, amino, methylamino, ethylamino, dimethylamino or diethylamino;

R$^2$ represents methyl, ethyl, methoxy, ethoxy, methylthio, ethylthio, amino, methylamino, ethylamino, dimethylamino or diethylamino;

R$^3$ represents methyl, ethyl, methoxy, ethoxy, methylthio, ethylthio, amino, methylamino, ethylamino, dimethylamino or diethylamino; and m represents the numbers 0, 1 or 2;

X represents methoxy, ethoxy, methylthio, ethylthio, amino, methylamino, ethylamino, dimethylamino or diethylamino;

X and R together with the carbon or nitrogen atom to which they are bonded represent a triazole radical of the formula

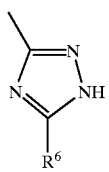

where

R$^6$ represents methyl, ethyl, hydroxyl, mercapto or amino;

Ar represents ortho-phenylene, pyridine-2,3-diyl or thiophene-2,3-diyl;

G represents oxygen, methylene or one of the groups which follow

—CH$_2$—O—, —O—CH$_2$—, —S(O)$_n$—, —CH$_2$—S(O)$_n$—, —S(O)$_n$—CH$_2$—, —C(R$^4$)=N—O—, —O—N=C(R$^4$)-, —C(R$^4$)=N—O—CH$_2$—, —O—C(R$^4$)=N—O—CH$_2$—, —NH—C(R$^4$)=N—O—CH$_2$—, —N(R$^5$)- or —CH$_2$—O—N=C(R$^4$)-, where n represents the numbers 0, 1 or 2, R$^4$ represents hydrogen, methyl or ethyl and R$^5$ represents hydrogen, methyl or ethyl;

Z represents in each case optionally substituted phenyl, pyridinyl, pyrimidinyl, pyridazinyl, pyrazinyl, 1,2,3-triazinyl, 1,2,4-triazinyl or 1,3,5-triazinyl, the substituents which are possible preferably being selected from the enumeration which follows:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, methylenedioxy or ethylenedioxy, each of which is optionally monosubstituted or polysubstituted by identical or different substituents from the series consisting of fluorine, chlorine, methyl or ethyl, or phenyl, phenoxy, benzyl or benzyloxy, each of which is optionally monosubstituted or polysubstituted in the phenyl moiety by identical or different substituents from the series consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy;

with the exception of the compounds excluded above by disclaimer.

A very particularly preferred group of compounds according to the invention are those compounds of the formula (I) in which Ar represents ortho-phenylene and R, X, G and Z have the meanings mentioned above in general, as preferred and as particularly preferred.

The abovementioned definitions of radicals, in general or in preferred ranges, apply to the end product of the formula (I) and analogously to the starting materials or intermediates required in each case for their preparation.

These definitions of radicals can be combined with each other as desired, that is to say combinations between the abovementioned ranges of preferred compounds are also possible.

Examples of the compounds according to the invention are given in Tables 1 to 42:

TABLE 1
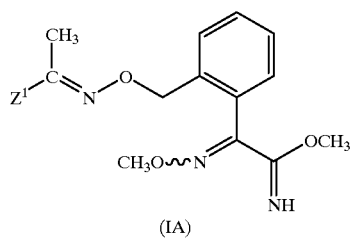
(IA)
in which Z¹ represents the following substituents
TABLE 2
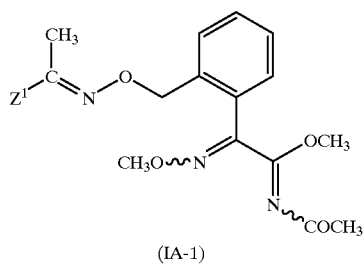
(IA-1)
in which Z¹ represents the substituents mentioned in Table 1.
TABLE 3
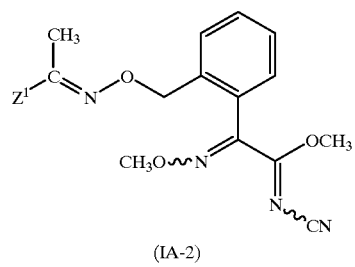
(IA-2)
in which Z¹ represents the substituents mentioned in Table 1.

TABLE 4

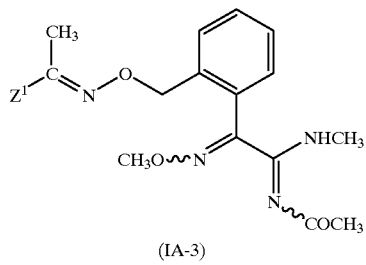

(IA-3)

in which Z¹ represents the substituents mentioned in Table 1.

TABLE 5

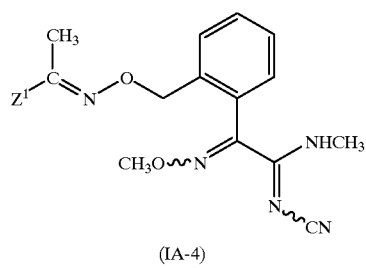

(IA-4)

in which Z¹ represents the substituents mentioned in Table 1.

TABLE 6

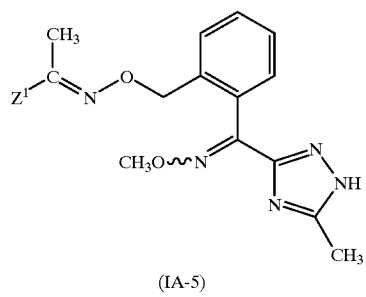

(IA-5)

in which Z¹ represents the substituents mentioned in Table 1.

TABLE 7

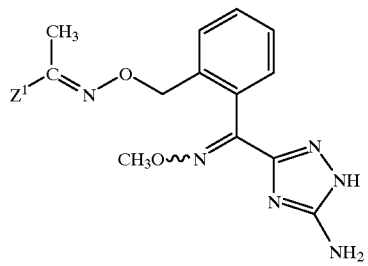

(IA-6)

in which Z¹ represents the substituents mentioned in Table 1.

TABLE 8

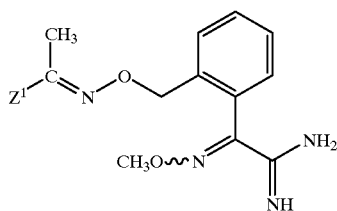

(IA-7)

in which Z¹ represents the substituents mentioned in Table 1.

TABLE 9

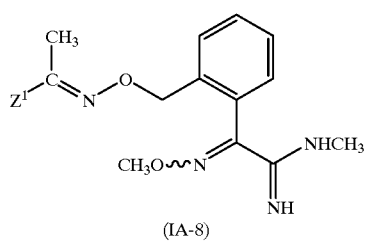

(IA-8)

in which Z¹ represents the substituents mentioned in Table 1.

TABLE 10
in which E represents the following substituents:

TABLE 10-continued
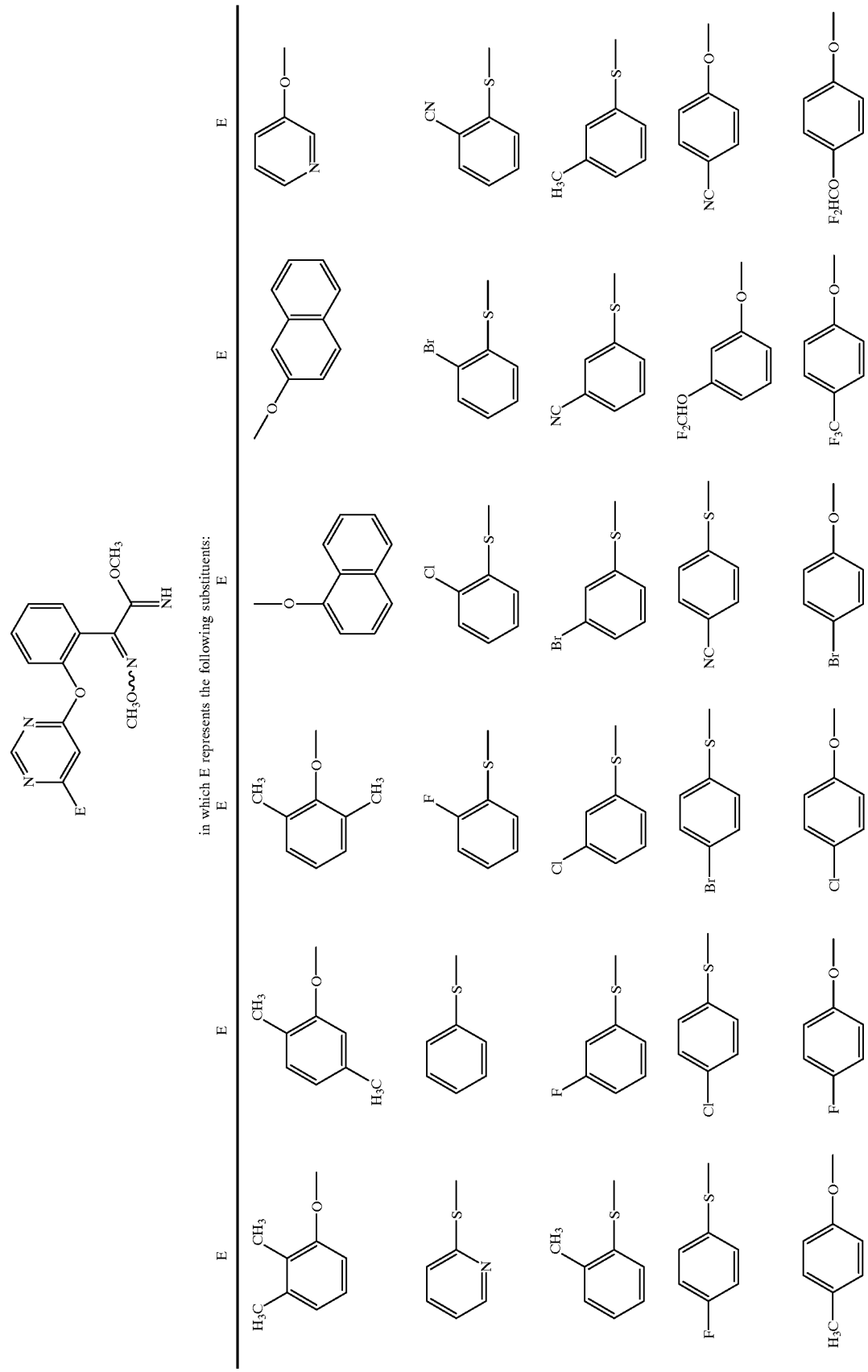

TABLE 10-continued
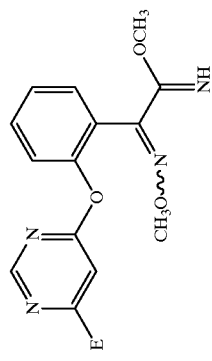
in which E represents the following substituents:
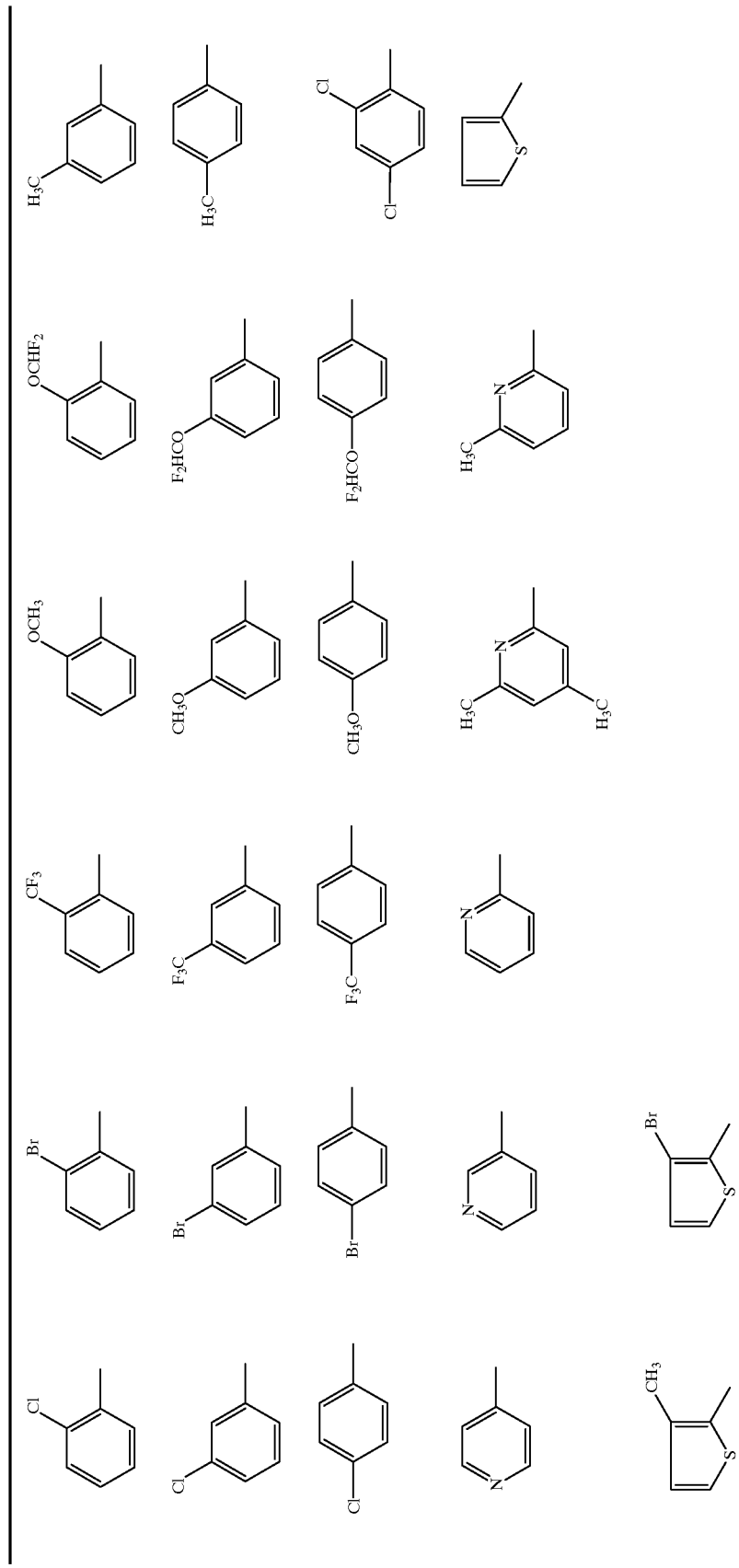

TABLE 11

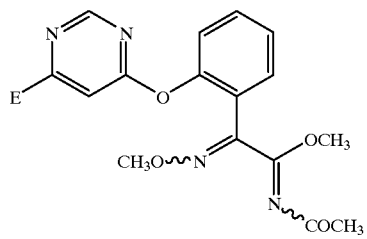

in which E represents the substituents given in Table 10.

TABLE 12

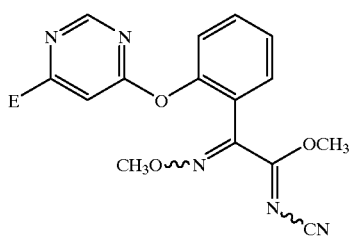

in which E represents the substituents given in Table 10.

TABLE 13

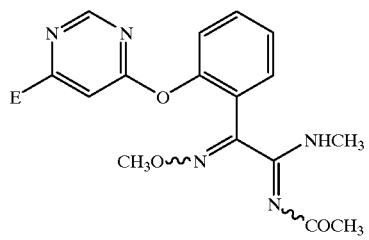

in which E represents the substituents given in Table 10.

TABLE 14

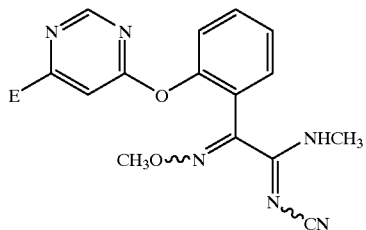

in which E represents the substituents given in Table 10.

TABLE 15

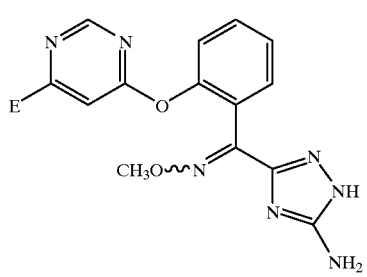

in which E represents the substituents given in Table 10.

TABLE 16

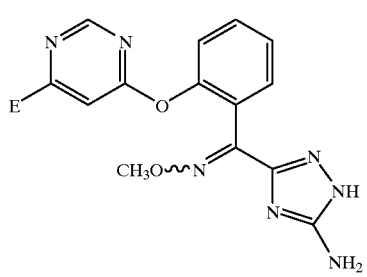

in which E represents the substituents given in Table 10.

TABLE 17

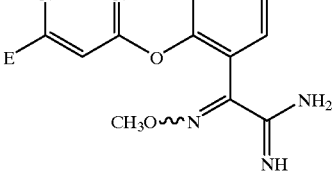

in which E represents the substituents given in Table 10.

TABLE 18

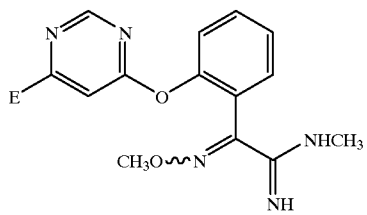

(IB-8)

in which E represents the substituents given in Table 10.

TABLE 19

(IC)

in which D represents the following substituents:

TABLE 19-continued
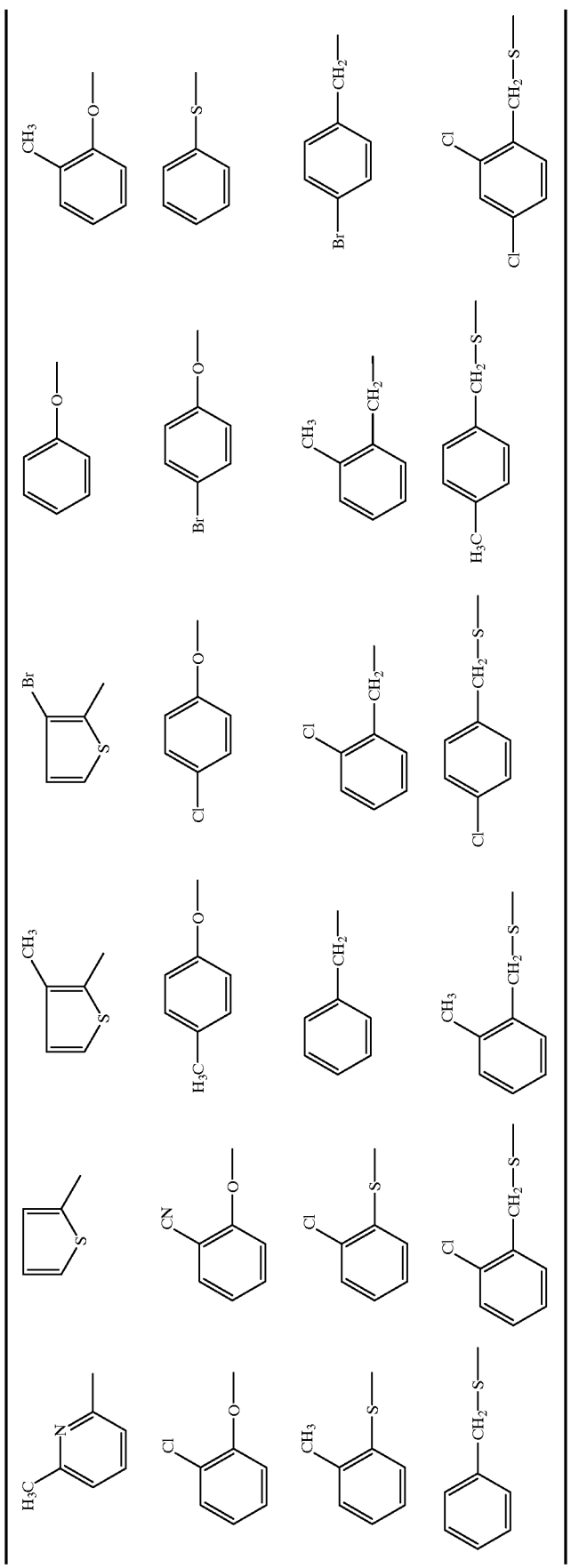

TABLE 20

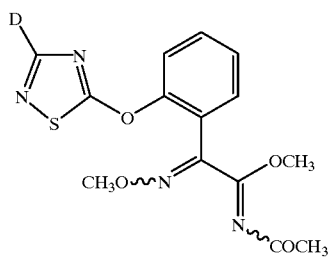 (IC-1)

in which D represents the substituents given in Table 19.

TABLE 21

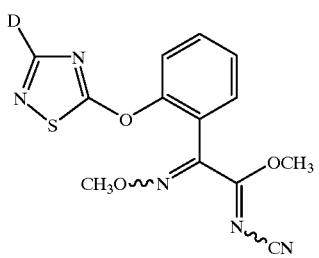 (IC-2)

in which D represents the substituents given in Table 19.

TABLE 22

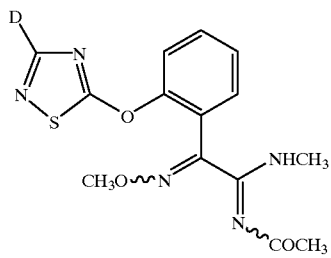 (IC-3)

in which D represents the substituents given in Table 19.

TABLE 23

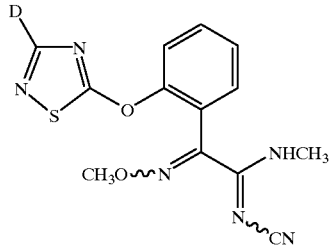 (IC-4)

in which D represents the substituents given in Table 19.

TABLE 24

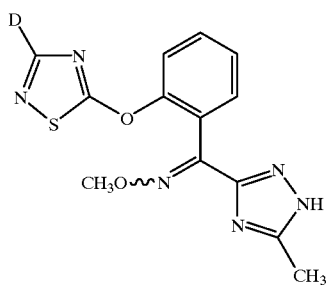 (IC-5)

in which D represents the substituents given in Table 19.

TABLE 25

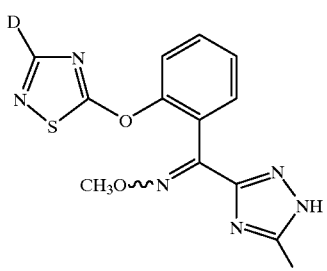 (IC-6)

in which D represents the substituents given in Table 19.

TABLE 26

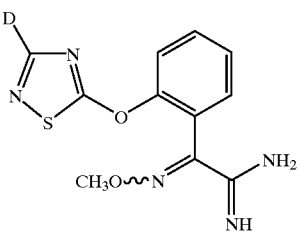 (IC-7)

in which D represents the substituents given in Table 19.

TABLE 27

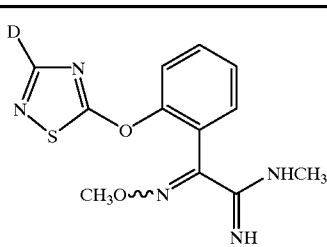 (IC-8)

in which D represents the substituents given in Table 19.

TABLE 28

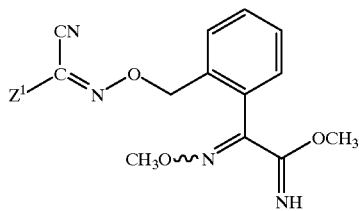
(ID)

in which Z¹ represents the substituents given in Table 1.

TABLE 29

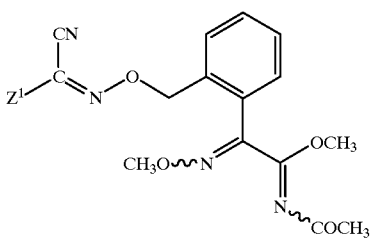
(ID-1)

in which Z¹ represents the substituents given in Table 1.

TABLE 30

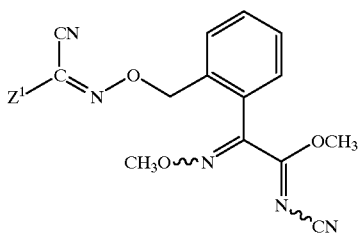
(ID-2)

in which Z¹ represents the substituents given in Table 1.

TABLE 31

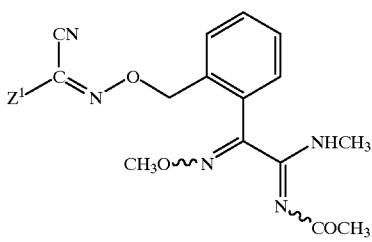
(ID-3)

in which Z¹ represents the substituents given in Table 1.

TABLE 32

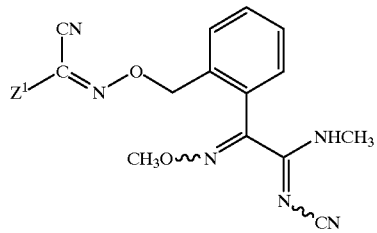
(ID-4)

in which Z¹ represents the substituents given in Table 1.

TABLE 33

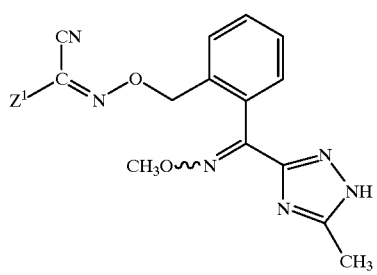
(ID-5)

in which Z¹ represents the substituents given in Table 1.

TABLE 34

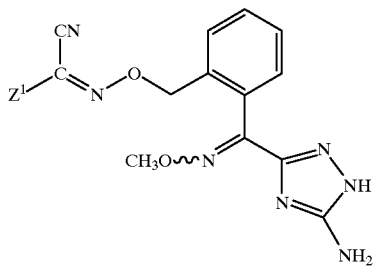
(ID-6)

in which Z¹ represents the substituents given in Table 1.

TABLE 35

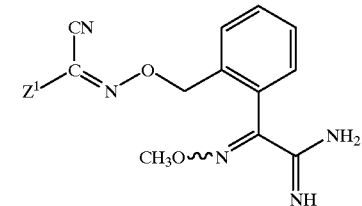
(ID-7)

in which Z¹ represents the substituents given in Table 1.

TABLE 36
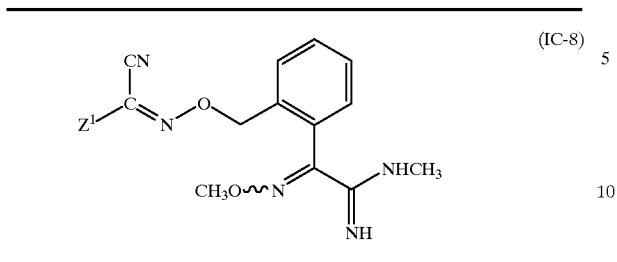
(IC-8)
in which $Z^1$ represents the substituents given in Table 1.
TABLE 37
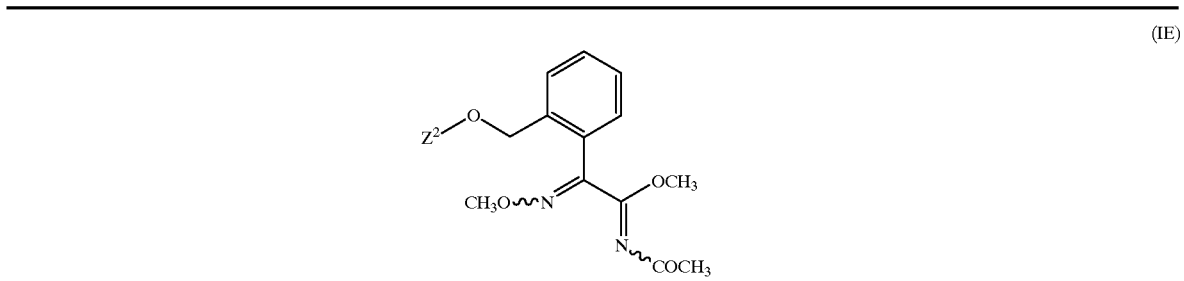
(IE)
in which $Z^2$ represents the following substituents:
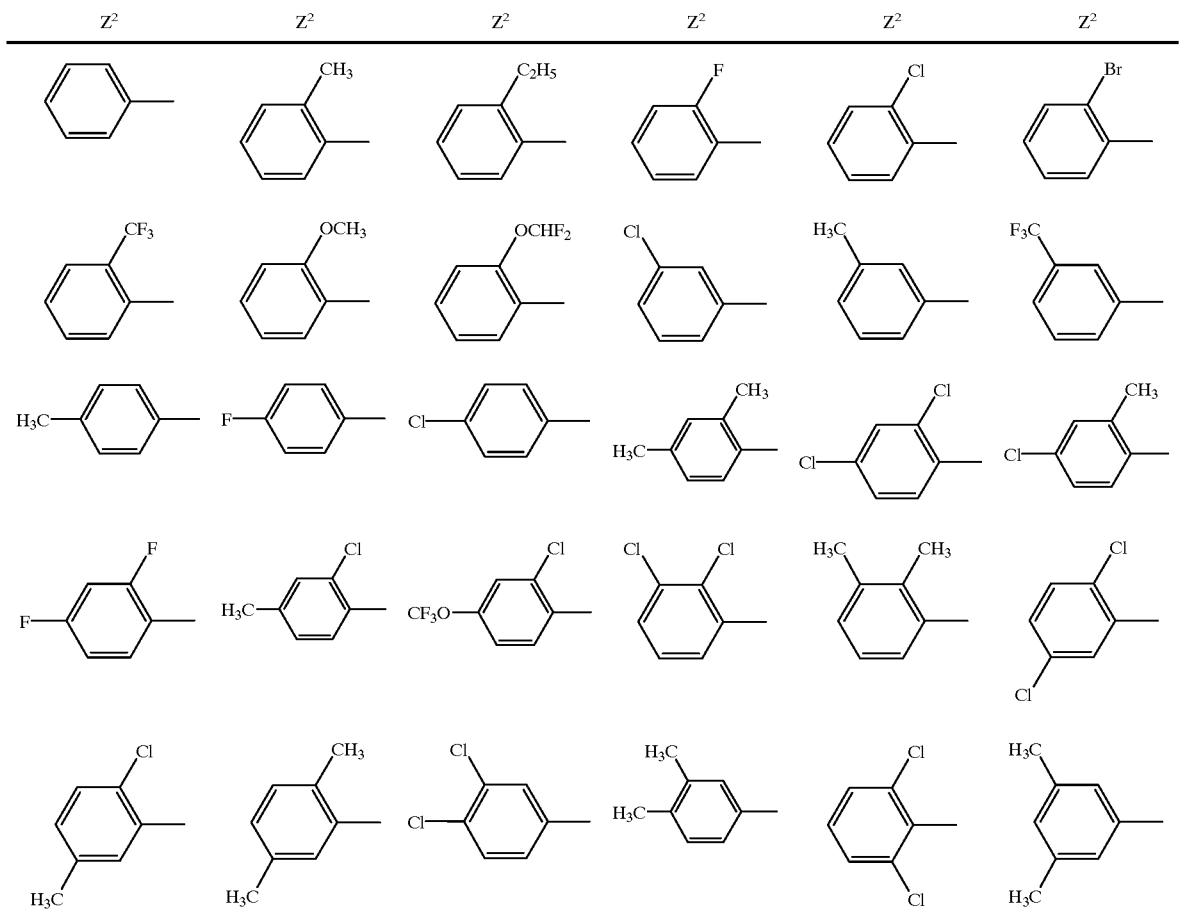

TABLE 37-continued

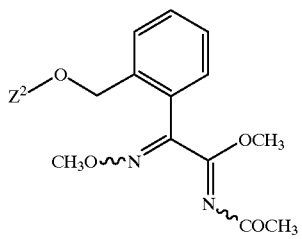

(IE)

in which $Z^2$ represents the following substituents:

| $Z^2$ | $Z^2$ | $Z^2$ | $Z^2$ | $Z^2$ | $Z^2$ |
|---|---|---|---|---|---|
| 1-naphthyl | 2-naphthyl | | | | |

TABLE 38

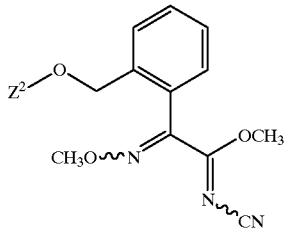

(IE-1)

in which $Z^2$ represents the substituents given in Table 1.

TABLE 39

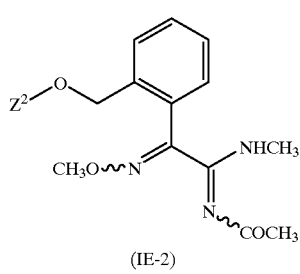

(IE-2)

in which $Z^2$ represents the substituents given in Table 1.

TABLE 40

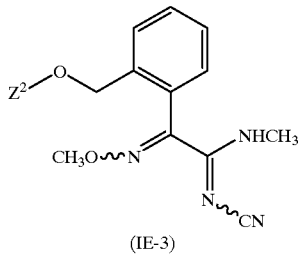

(IE-3)

in which $Z^2$ represents the substituents given in Table 1.

TABLE 41

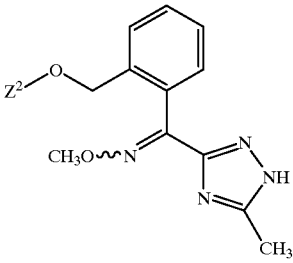

(IE-4)

in which $Z^2$ represents the substituents given in Table 1.

TABLE 42

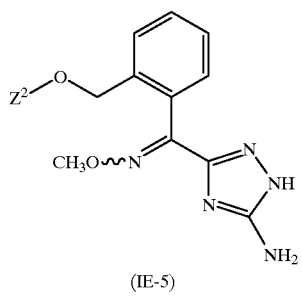

(IE-5)

in which $Z^2$ represents the substituents given in Table 1.

Formula (II) provides a general definition of the nitrites required as starting substances for carrying out process (a) according to the invention. In formula (II), Ar, G and Z preferably or particularly preferably have those meanings which have already been mentioned above in connection with the description of the compounds of the formula (I) as being preferred or particularly preferred for these substituents.

The nitrites of the formula (II) were hitherto unknown; however, they can be prepared in a generally known manner by reacting amides of the general formula (VII)

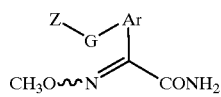

(VII)

in which
Ar, G and Z have the abovementioned meanings
with dehydrating agents, such as, for example, anhydrides, at temperatures between 0 and 100° C., preferably between 0 and 50° C., if appropriate in the presence of a reaction auxiliary, such as, for example, pyridine (cf. also the preparation examples).

The amides of the formula (VII) are known (cf., for example, EP-A 0 398 692) or can be prepared in a generally known manner by the processes described therein, for example by reacting suitable ester derivatives (cf., in this context, for example EP-A 0 253 213, EP-A 0 506 149, EP-A 0 463 488 or EP-A 0 398 692) with ammonia (cf. in this context also the preparation examples).

Ester derivatives of the general formula (IX)

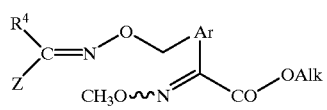

(IX)

in which
Ar, $R^4$ and Z have the abovementioned meanings and
Alk represents alkyl, preferably $C_1$–$C_4$-alkyl such as, in particular, methyl, can also be obtained by first reacting ester derivatives of the general formula (X) (cf., for example, EP-A 0 506 149 and EP-A 0 600 835)

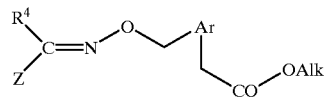

(X)

in which
Ar, Alk, $R^4$ and Z have the abovementioned meanings
in a known manner with a nitrosating agent, such as, for example, n-butyronitrile, in a suitable solvent, such as, for example, tert-butanol and in the presence of a suitable base, such as, for example, potassium tert-butylate, to give the corresponding oxime derivatives of the general formula (Xa)

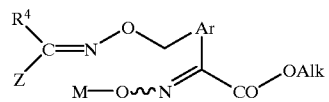

(Xa)

in which
Ar, Alk, $R^4$ and Z have the abovementioned meanings and
M represents hydrogen or a metal equivalent such as, in particular, potassium or sodium;
and these are subsequently
either directly converted into the ester derivatives of formula (IX) in the customary manner by means of alkylation,
or, after the oximes of the formula (Xa) where M=hydrogen have been freed and isolated, converted into the ester derivatives of the formula (IX) using a base, such as, for example, potassium carbonate, and an alkylating agent, such as, for example, dimethyl sulphate, in the presence of a suitable solvent, such as, for example, acetonitrile (cf. also the preparation examples).

The ester derivatives of the general formula (X) can be obtained by first (step 1) converting an oxime of the general formula (XI)

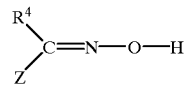

(XI)

in which
$R^4$ and Z have the abovementioned meanings
into the corresponding salt at temperatures between –20° C. and 200° C. by means of a base, such as, for example, alkali metal alcoholates or metal hydrides, in particular sodium hydride and potassium tert-butanolate, if appropriate in the presence of a diluent, such as, for example, methanol, ethanol, dimethylformamide or N-methylpyrrolidone, and reacting the product at the same temperature with a dichloro derivative of the general formula (XII)

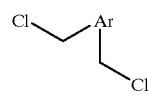

(XII)

in which
Ar has the abovementioned meanings
to give an 0-iminooxymethyl derivative of the general formula (XIII)

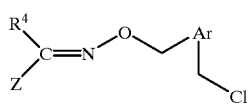

(XIII)

in which

Ar, R⁴ and Z have the abovementioned meanings, it being possible for the dichloro derivative of the formula (XII) to be employed in equivalent amounts, but also in any excess, preferably an excess of 1 to 10 equivalents; subsequently (step 2) reacting the resulting O-iminooxymethyl derivatives of the formula (XIII) with 1 to 5, preferably 1 to 1.1, equivalents of alkali metal cyanide in the presence of a diluent, such as, for example, acetone, acetonitrile, methyl ethyl ketone, dimethyl sulphoxide, toluene, methanol, ethanol, isopropanol, butanol, tetrahydrofuran, dioxane or water, at temperatures between 0° C. and 100° C., preferably between 20° C. and 50° C., if appropriate in the presence of a phase transfer catalyst, such as, for example, tetra-n-butylammonium chloride, tetra-n-butylammonium bromide, tetra-n-butylammonium hydrogen sulphate, tetra-methylammonium bromide or benzyltri-ethylammonium chloride, to give an acetonitrile derivative of the general formula (XIV)

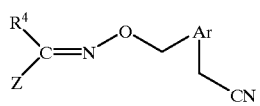

(XIV)

in which

Ar, R⁴ and Z have the abovementioned meanings;

and subseqently (step 3)

either reacting the resulting acetonitrile derivatives of the formula (VIV) directly in a generally known manner with alcohol in the presence of an aqueous acid to give the ester derivatives of the formula (X);

or first converting the resulting acetonitrile derivatives of the formula (XIV) in a generally customary manner into the corresponding acetic acid derivatives of the general formula (XV)

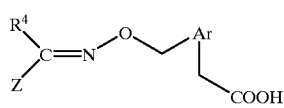

(XV)

in which

Ar, R⁴ and Z have the abovementioned meanings by means of hydrolysis in the presence of strong bases or mineral acids and subsequently reacting them in the generally customary manner with alcohol in the presence of an acid or a base to give the ester derivatives of the formula (X); or first converting the resulting acetonitrile derivatives of the formula (XIV) in a generally customary manner into the corresponding acetyl halide derivatives of the general formula (XVI)

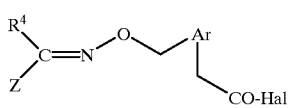

(XVI)

in which

Ar, R⁴ and Z have the abovementioned meanings and

Hal represents halogen, preferably chlorine or bromine, in particular chlorine, by means of an acid halide, such as, in particular, PCl₃, PCl₅, POCl₃, SOCl₂ or SO₂Cl₂, and subsequently reacting them in the generally customary manner with alcohol, if appropriate in the presence of an acid-binding agent, to give the ester derivatives of the formula (X).

(cf. also the preparation examples)

The oximes of the formula (XI) and the dichloro derivatives of the formula (XII) are generally known compounds of organic chemistry and can be prepared in the generally customary manner.

The O-iminooxymethyl derivatives of the formula (XIII), the acetonitrile derivatives of the formula (XIV), the acetic acid derivatives of the formula (XV) and the acetyl halide derivatives of the formula (XVI) are new and also provided by the present invention.

Nitriles of the formula (IIa)

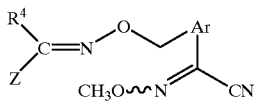

(IIa)

in which

Ar, R⁴ and Z have the abovementioned meanings can also be obtained by reacting 2-methoximino-2-(2-bromomethylphenyl)acetonitrile of the formula (XVII)

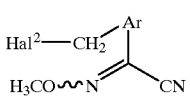

(XVII)

in which

Hal² represents halogen and

Ar has the abovementioned meanings with oxime derivatives of the general formula (XVIII)

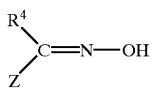

(XVIII)

in which

R⁴ and Z have the abovementioned meanings, if appropriate in the form of their alkali metal salts, at temperatures between 0 and 100° C., preferably between 0 and 80° C., in the presence of a diluent, such as, for example, dimethylformarnide, and if appropriate in the presence of a base, such as, for example, sodium hydride or potassium hydride (cf. also the preparation examples).

The 2-methoximinoacetonitriles of the formula (XVII) are obtained by first converting 2-methoximinoacetic esters of the formula (XIX)

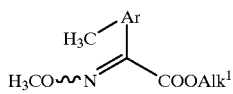
(XIX)

in which
Ar has the abovementioned meanings and
$Alk^1$ represents methyl or ethyl
with ammonia in the generally customary manner into a 2-methoximinoacetamide of the formula (XX)

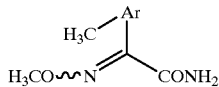
(XX)

in which
Ar has the abovementioned meanings;
the product is reacted with dehydrating agents, such as, for example, anhydrides, if appropriate in the presence of a reaction auxiliary, such as, for example, pyridine, at temperatures between 0 and 100° C., preferably between 0 and 50° C., to give a nitrile derivative of the formula (XXI)

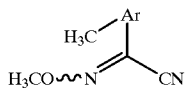
(XXI)

in which
Ar has the abovementioned meanings;
and finally brominating the resulting nitrile derivative of the formula (XXI), for example by reaction with N—bromosuccinimide in the presence of a catalyst, such as, for example, dibenzoyl peroxide (cf. also the preparation examples).

The compounds of the formulae (XVII), (XX) and (XXI) are new and also provided by the present invention.

The oxime derivatives of the general formula (XVIII) are known (cf., for example, Houben-Weyl "Methoden der organischen Chemie" [Methods in Organic Chemistry], Volume VII/I, p. 413–488) or can be obtained in the generally customary manner.

The methyl 2-methoximinoacetates of the formula (XIX) are known and/or can be prepared by known methods (cf., for example, EP-A 0 400 417).

Formula (III) provides a general definition of the (thio) alcohols furthermore required as starting materials for carrying out process (a) according to the invention. In formula (III), $X^1$ preferably, or particularly preferably, has those meanings which have already been mentioned above in connection with the description of the compounds of the formula (I) as being preferred or particularly preferred for X in its meaning of alkoxy or alkylthio.

The (thio) alcohols of the formula (III) and their alkali metal salts, such as, for example, sodium and potassium salts, are generally known compounds of organic chemistry.

Formula (Ia) provides a general definition of the imidates which are required as starting materials for carrying out processes (b), (c) and (f) according to the invention. In formula (Ia), Ar, G, Z and $X^1$ (for X in its meaning of alkoxy or alkylthio) preferably or particularly preferably have those meanings which have already been mentioned above in connection with the description of the compounds of the formula (I) as being preferred or particularly preferred for these substituents.

The imidates of the formula (Ia) are compounds according to the invention and can be obtained in accordance with process (a).

Imidates of the formula (Ia) in which $X^1$ represents alkylthio can also be obtained by reacting amides of the general formula (VII) with a sulphurizing agent, such as, for example, $P_4S_{10}$ or Lawesson reagent, at temperatures between 50° C. and 200° C., if appropriate in a diluent, such as, for example, toluene or xylene, and alkylating the resulting thioamides of the general formula (VIII)

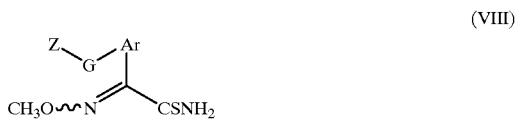
(VIII)

in which
Ar, G and Z have the abovementioned meanings
in the customary manner.

Formula (IV) provides a general definition of the acid halides furthermore required as starting substances for carrying out process (b) according to the invention. In formula (IV), R preferably, or particularly preferably, has those meanings which have already been mentioned above in connection with the description of the compounds of the formula (I) as being preferred, or particularly preferred, for this substituent. Hal preferably represents fluorine, chlorine or bromine, particularly preferably chlorine.

The acid halides of the formula (IV) are generally known compounds of organic chemistry.

Cyanamide, of the formula (V), which is furthermore required as starting material for carrying out process (c) according to the invention, is equally a generally known compound of organic chemistry.

Formula (Ib) provides a general definition of the imidic acid derivatives required as starting material for carrying out process (d) according to the invention. In formula (Ib), Ar, G, Z, $X^1$ (for X in its meaning of alkoxy or alkylthio) and R' (for R in its abovementioned meaning with the exception of hydrogen) preferably or particularly preferably have those meanings which have already been mentioned above in connection with the description of the compounds of the formula (I) as being preferred, or particularly preferred, for these substituents.

The imidic acid derivatives of the formula (Ib) are compounds according to the invention and can be obtained in accordance with processes (b) and (c).

Formula (VI) provides a general definition of the amines furthermore required as starting materials for carrying out processes (d) and (f) according to the invention. In formula (VI), X preferably, or particularly preferably, has those meanings which have already been mentioned above in connection with the description of the compounds of the formula (I) as being preferred, or particularly preferred, for X in its meaning of amino, alkylamino and dialkylamino.

The amines of the formula (VI) are generally known compounds of organic chemistry.

Formula (Ic) provides a general definition of the imidic acid derivatives required as starting material for carrying out process (e) according to the invention. In formula (Ic), Ar, G, Z and R' (for R in its abovementioned meaning with the exception of hydrogen) preferably, or particularly preferably, have those meanings which have already been mentioned above in connection with the description of the compounds of the formula (I) as being preferred, or particularly preferred, for these substituents.

The imidic acid derivatives of the formula (Ic) are compounds according to the invention and can be obtained in accordance with processes (b) and (c).

Hydrazine, or hydrazine hydrate, which is furthermore required as starting material for carrying out process (e) according to the invention is a generally known compound of organic chemistry.

Diluents which are suitable for carrying out process (a) according to the invention are all inert organic solvents which are customary for such reactions. The following can preferably be used: ethers, such as diethyl ether, methyl tert-butyl ether, dioxane, tetrahydrofuran, ethylene glycol dimethyl ether or ethylene glycol diethyl ether; furthermore nitriles, such as acetonitrile; and furthermore optionally halogenated aliphatic, cycloaliphatic and aromatic hydrocarbons, such as methylene chloride, chloroform, carbon tetrachloride, hexane, cyclohexane, benzene, toluene, xylene, chlorobenzene and petroleum ether.

Process (a) according to the invention is preferably carried out in the presence of a suitable reaction auxiliary. Suitable reaction auxiliaries are all inorganic and organic bases which can conventionally be used. The following are preferably used: the hydrides, hydroxides, alcoholates, acetates, carbonates or hydrogen carbonates of alkali metals, such as, for example, sodium hydroxide, sodium methylate, sodium ethylate, potassium t-butylate, sodium acetate, potassium acetate, sodium carbonate, potassium carbonate or sodium hydrogen carbonate, or else tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU). If appropriate, acidic reaction auxiliaries, such as, for example, p-toluene-sulphonic acid, may also be advantageous.

When carrying out process (a) according to the invention, the reaction temperatures can be varied within a substantial range. In general, the process is carried out at temperatures between 0° C. and 200° C., preferably at temperatures between 0° C. and 100° C.

To carry out process (a) according to the invention, 1 to 10 mol, preferably 1 to 5 mol, of (thio) alcohol of the formula (III) or an alkali metal salt thereof and, if appropriate, 1 to 10 mol, preferably 1 to 5 mol, of reaction auxiliary are generally employed per mol of nitrile of the formula (II). However, a large excess is also possible.

Suitable diluents for carrying out process (b) according to the invention are all inert organic solvents. The following can preferably be used: aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride; ethers, such as diethyl ether, dioxane, tetrahydrofuran, ethylene glycol dimethyl ether or ethylene glycol diethyl ether, or esters, such as ethyl acetate.

Process (b) according to the invention is preferably carried out in the presence of a suitable reaction auxiliary. Suitable reaction auxiliaries are all inorganic and organic bases which can conventionally be used. The following are preferably used: the hydrides, hydroxides, alcoholates, acetates, carbonates or hydrogen carbonates of alkali metals, such as, for example, sodium hydroxide, sodium methylate, sodium ethylate, potassium t-butylate, sodium acetate, potassium acetate, sodium carbonate, potassium carbonate or sodium hydrogen carbonate, or else tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out process (b) according to the invention, the reaction temperatures can be varied within a substantial range. In general, the process is carried out at temperatures between 0° C. and 150° C., preferably at temperatures between 0° C. and 100° C.

To carry out process (b) according to the invention, 0.8 to 5 mol, preferably 0.8 to 3 mol. of acid derivative of the formula (IV) and, if appropriate, 1 to 5 mol, preferably 1 to 3 mol, of reaction auxiliary are generally employed per mol of imidate of the formula (Ia).

Suitable diluents for carrying out process (c) according to the invention are water and all organic solvents which are miscible with water including their mixtures with water. Diluents which may preferably be mentioned are alcohols, such as, for example, methanol or ethanol.

Process (c) according to the invention is preferably carried out in the presence of a suitable reaction auxiliary. Suitable reaction auxiliaries are preferably inorganic salts, such as the acetates, carbonates, hydrogen carbonates, phosphates, hydrogen phosphates or dihydrogen phosphates of alkali metals, such as, for example, sodium acetate, potassium acetate, sodium carbonate, potassium carbonate, sodium hydrogen carbonate, sodium phosphate, sodium dihydrogen phosphate and disodium hydrogen phosphate.

When carrying out process (c) according to the invention, the reaction temperatures can be varied within a substantial range. In general, the process is carried out at temperatures between −20° C. and +100° C., preferably at temperatures between 0° C. and 50° C.

To carry out process (c) according to the invention, 0.5 to 5 mol, preferably 0.5 to 2 mol, of cyanamide of the formula (V) and, if appropriate, 2 to 20 mol, preferably 2 to 8 mol, of reaction auxiliary are generally employed per mol of imidate of the formula (Ia), and the pH of the reaction mixture should generally be between 4 and 9, preferably between 6 and 7.

Diluents for carrying out processes (d) and (e) according to the invention are water and all inert organic solvents which are miscible with water. The following can preferably be used: ethers, such as dioxane, tetrahydrofuran, ethylene glycol dimethyl ether or ethylene glycol diethyl ether, nitrites, such as acetonitrile or propionitrile, amides, such as dimethylformamide, dimethylacetamide, N-methylformamide, N-methylpyrrolidone or hexamethylphosphoramide, or sulphoxides, such as dimethyl sulphoxide, alcohols, such as methanol or ethanol, or basic solvents, such as pyridine or triethylamine.

When carrying out processes (d) and (e) according to the invention, the reaction temperatures can be varied within a substantial range. In general, the process is carried out at temperatures between −50° C. and +100° C., preferably at temperatures between −20° C. and +50° C.

Process (d) according to the invention is preferably carried out using molar amounts; however, it is also possible to employ a large excess of the amine of the formula (VI).

To carry out process (e) according to the invention, 0.5 to 10 mol, preferably 0.5 to 5 mol, of hydrazine or hydrazine hydrate are generally employed per mol of imidic acid derivative of the formula (Ic).

Suitable diluents for carrying out process (f) according to the invention are water and polar organic solvents. The following can preferably be used: ethers, such as diethyl ether, dioxane, tetrahydrofuran, ethylene glycol dimethyl ether or ethylene glycol diethyl ether, and also alcohols, such as methanol or ethanol. However, the amine of the formula (VI) to be employed as reactant may also be used.

When carrying out process (f) according to the invention, the reaction temperatures can be varied within a substantial range. In general, the process is carried out at temperatures between −40° C. and +200° C., preferably at temperatures between 0C and 100° C.

Process (f) according to the invention is preferably carried out using molar amounts; however, it is also possible to employ a larger excess, in particular of the amine of the formula (VI).

Processes (a) to (f) according to the invention are generally carried out under atmospheric pressure. However, it is also possible to carry out the process under reduced or, in particular, elevated pressure.

The reaction is carried out and the reaction products are worked up and isolated by generally customary methods (cf. also the preparation examples).

The active compounds of the formula (I) according to the invention have a powerful microbicidal action and can be used in practice for combating undesired microorganisms. The active compounds are suitable for use as plant protection substances, in particular as fungicides.

Fungicidal agents in plant protection are employed for combating Plasmo-diophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Peronospora species, such as, for example, *Peronospora pisi* or *Peronospora brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *Pyrenophora graminea* (conidia form: Drechslera, syn: Helnthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae* and
Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be employed particularly successfully for combating diseases in fruit and vegetable growing, such as, for example, against Podosphaera and Venturia species, for combating cereal diseases, such as, for example against Erysiphe species, or for combating rice diseases, such as, for example, against Pyricularia oryzae.

Depending on their particular physical and/or chemical properties, the active compounds can be converted into customary formulations, such as solutions, emulsions, suspensions, powders, foams, pastes, granules, aerosols, very fine capsules in polymeric substances and in coating compositions for seed, as well as ULV cold and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methyl cellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

The active compounds according to the invention, as such or in their formulations, can also be used in the form of a mixture with known fungicides, bactericides, acaricides, nematicides or insecticides, for example to widen the spectrum of action or to prevent the build-up of resistance.

Examples of suitable substances for mixtures are the following:

Fungicides:
2-aminobutane; 2-anilino-4-methyl-6-cyclopropyl-pyrimidine; 2',6'-dibromo-2-methyl-4'-trifluoromethoxy-4'-trifluoro-methyl-1,3-thizole-5-carboxanilide; 2,6-di-chloro—N-(4-trifluoromethylbenzyl)benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyriridin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole,
benalaxyl, benodanil, benomyl, binapacryl, biphenyl, bitertanol, blasticidin—S, bromuconazole, bupirimate, buthiobate,
calcium polysulphide, captafol, captan, carbendazim, carboxin, quinomethionate, chloroneb, chloropicrin, chlorothalonil, chlozolinate, cufraneb, cymoxanil, cyproconazole, cyprofuram,
dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon,
edifenphos, epoxyconazole, ethirimol, etridiazole,
fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine,
hexachlorobenzene, hexaconazole, hymexazol,
imazalil, imibenconazole, iminoctadine, iprobenfos (IBP), iprodione, isoprothiolane,
kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin,
pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon,
quintozene (PCNB),
sulphur and sulphur preparations,
tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole,
validamycin A, vinclozolin,
zineb, ziram Bactericides:
bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin,
Bacillus thuringiensis, bendiocarb, benfuracarb, bensultap, betacyfluthrin, bifenthrin, BPMC, brofenprox, bromophos A, bufencarb, buprofezin, butocarboxin, butylpyridaben,
cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton-K demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, etrimphos,
fenarniphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mevinphos, mesulfenphos, metaldehyde, methacrifos, methamidophos, methidathion, methiocarb, methomyl, metolcarb, milbemectin, monocrotophos, moxidectin,
naled, NC 184, NI 25, nitenpyram,
omethoate, oxamyl, oxydemethon M, oxydeprofos,
parathion A, parathion M, permetlrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyraclofos, pyridaphenthion, pyresmethrin, pyrethrum, pyridaben, pyrimidifen, pyriproxifen, quinalphos,
RH 5992,
salithion, sebufos, silafluofen, sulfotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, YI 5301/5302, zetamethrin.

A mixture with other known active compounds, such as herbicides, or with fertilizers and growth regulators, is also possible.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

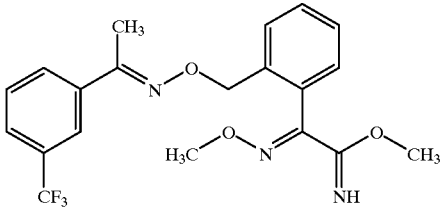

(Process a)

A solution of 11.3 g (0.03 mol) of E-2-methoximino-2-{2-[1-(3-trifluoromethylphenyl)-ethylideneiminooxymethyl]-phenyl}-acetonitrile and 13.0 g (0.24 mol) of sodium methanolate in 46 ml of methanol is stirred at room temperature for 48 hours. The solution is poured into 3 l of water, extracted with ether, dried using potassium carbonate and concentrated. 12.2 g of a pale yellow oil containing 80% (GC) of methyl E-2-methoximino-2-{2-[1-(3-trifluoromethyl-phenyl)-ethytideneiminooxy-methyl]-phenyl}-acetimidate are obtained.

$^1$H NMR (CDCl$_3$): d=2.22; 3.86: 3.99; 5.11: 7.11–7.95.

Preparation of the starting material (Variant 1)

(II-1)

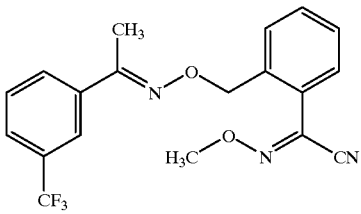

A solution of 2.8 g (0.007 mol) of E-2-methoximino-2-{2-[1-(3-trifluoro-methyl-phenyl)-ethylideneiminooxymethyl]-phenyl}-acetamide in 5 ml of pyridine is cooled to 0° C., 2.2 g (0.0105 mol) of trifluoroacetic anhydride are added, and the mixture is stirred at 0° C. for 2 hours and room temperature for 18 hours. The solution is concentrated, the residue is taken in ethyl acetate, and the mixture is washed with water and highly dilute hydrochloric acid, dried using magnesium sulphate and concentrated. The residue is chromatographed on silica gel using cyclohexane/ethyl acetate (3:1). 1.8 g (69%) of E-2-methoximino-2-{2-[1-(3-trifluoro-methylphenyl)-ethylideneiminooxymethyl]-phenyl}-acetonitrile are obtained as a yellow oil (IR spectrum: 2200 cm$^{-1}$).

(VII-1)

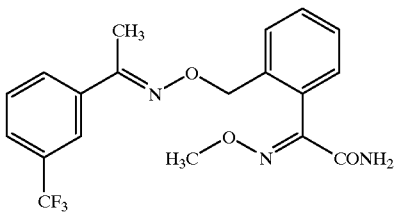

Ammonia is passed into a solution of 32.6 g (0.08 mol) of methyl E-2-methoximino-2-{2-[1-(3-trifluoromethylphenyl)-ethylideneiminooxymethyl]-phenyl}-acetate in 200 ml of methanol at approximately 10° C. until the mixture is saturated. Stirring is continued for 2 hours, and the mixture is then concentrated. The residue is stirred with hexane and filtered off with suction. 23.8 g (76%) of E-2-methoximino-2-{2-[1-(3-trifluoromethylphenyl)-ethylideneiminooxymethyl]-phenyl}-acetamide of melting point 112° C. are obtained.

(IX-1)

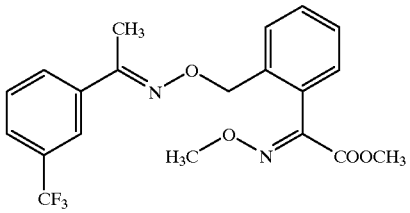

19.1 g (0.094 mol) of 3-trifluoromethylacetophenone oxime are added to a suspension of 4.5 g (0.113 mol) of sodium hydride in 80 ml of dimethylformamide, and the mixture is stirred until the evolution of gas has ceased. Then, 26.9 g (0.094 mol) of methyl E-2-methoximino-2-(2-bromomethylphenyl)-acetate are added and the mixture is stirred at room temperature overnight. The solvent is distilled off, the residue is poured into 1 l of water, and the mixture is extracted with ether. The organic phase is dried using magnesium sulphate and concentrated. 34.2 g (89%) of methyl E-2-methoximino-2-{2-[1-(3-trifluoromethylphenyl)-ethylideneiminooxy-methyl]-phenyl}-acetate are obtained as a brown oil.

Alternative preparation of the compound (IX-1)

Step 1

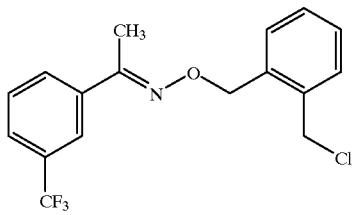
(XIII-1)

6.1 g (0.03 mol) of 3-trifluoromethylacetophenone oxime are dissolved in 30 ml of dimethylformamide and converted into the salt by adding 1.2 g (0.03 mol) of 60% sodium hydride at room temperature and stirring for 30 minutes. This salt solution is added dropwise to 21 g (0.12 mol) of α,α-dichloroxylene, which has been dissolved in 50 ml of dimethylformamide. The reaction mixture is heated at 50° C. for 1 hour and distilled under a high vacuum. After dimethylformamide and excess α,α-dichloroxylene has been distilled off, 8.4 g (81.9% of theory) of 2-[1-(3-trifluoromethylphenyl)-ethylideneiminooxymethyl]-benzyl chloride distil over at 0.3 Torr and 151 to 156° C.

$^1$H NMR spectrum (CDCl$_3$/TMS):

δ=2.249 (3H); 4.751 (2H); 5.393 (2H); 7.299–7.39 (2H); 7.39–7.462 (3H); 7.563/7.589 (1H); 7.784/7.811 (1H); 7.895 (1H) ppm.

Step 2

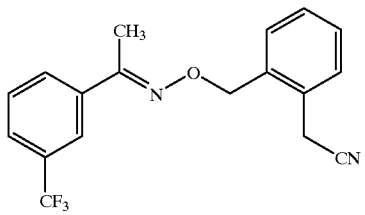
(XIV-1)

63.8 g (0.187 mol) of 2-[1-(3-trifluoromethylphenyl)-ethylideneiminooxymethyl]-benzyl chloride are added to 10.1 g (0.206 mol) of sodium cyanide in 200 ml of dimethyl sulphoxide and the mixture is stirred at room temperature for 12 hours. It is poured into water, extracted with ethyl acetate, the organic phase is concentrated, and the residue is stirred with low-boiling petroleum ether. 43 g (69.2% of theory) of 2-[1-(3-trifluoromethylphenyl)-ethylideneiminooxymethyl]-phenylacetonitrile are obtained.

$^1$H NMR spectrum (CDCl$_3$/TMS):

δ=2.263 (3H); 3.899 (2H); 5.278 (2H); 7.249–7.506 (5H); 7.597/7.623 (1H); 7.788/7.814 (1H); 7.885 (1H) ppm.

Step 3

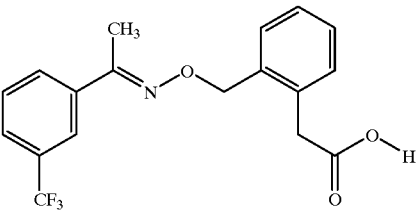
(XV-1)

15 g (0.045 mol) of 2-[1-(3-trifluoromethylphenyl)-ethylideneiminooxymethyl]-phenyl-acetonitrile are stirred at 140° C. for 7 hours with 90 ml of ethylene glycol and 7 g (0.106 mol) of 85% KOH powder. The mixture is poured into water and extracted with ethyl acetate. The mixture is then acidified and the product is extracted using dichloromethane. After the solvent has been stripped off, 13 g (82.2% of theory) of acid are obtained.

$^1$H NMR spectrum (CDCl$_3$/TMS):

δ=2.181 (3H); 3.826 (2H); 5.291 (2H); 7.248–7.339 (3H); 7.421–7.468 (2H); 7.570/7.596 (1H); 7.761/7.787 (1H); 7.858 (1H) ppm.

Step 4

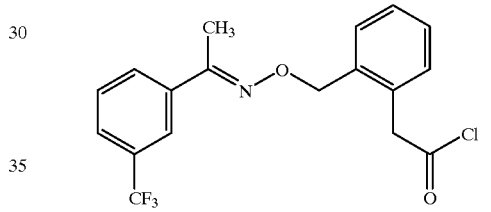
(XVI-1)

3.5 g (0.05 mol) of 2-[1-(3-trifluoromethylphenyl)-ethylideneiminooxymethyl]-phenyl-acetic acid are refluxed for 2 hours with 10 ml of dichloroethane and 1.4 g (0.012 mol) of thionyl chloride. After the volatile components have been stripped off, 3.5 g (94.7% of theory) of crude 2-[1-(3-trifluoromethylphenyl)-ethylideneiminooxymethyl]-phenylacetyl chloride are obtained.

$^1$H NMR spectrum (CDCl$_3$/TMS):

δ=2.236 (3H); 4.334 (2H); 5.268 (2H); 7.249–7.291 (1H); 7.357–7.387 (2H); 7.436–7.501 (2H); 7.593/7.619 (1H); 7.793–7.819 (1H); 7.896 (1H) ppm.

Step 5

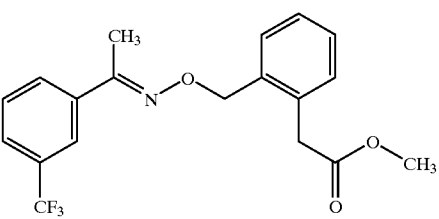
(X-1)

2.4 g (6.5 mmol) of 2-[1-(3-trifluoromethylphenyl)-ethylideneiminooxymethyl]-phenyl-acetyl chloride are added at 25° C. with cooling to a mixture of 10 ml of methanol and 0.7 g (6.9 mmol) of triethylamine. After 10 minutes at room temperature, the mixture is concentrated, and the residue is partitioned between ethyl acetate and water. After the solvent has been stripped off, 2 g (84.3% of theory) of methyl 2-[1-(3-trifluoromethylphenyl)-ethylideneiminooxymethyl]-phenylacetate are obtained. GCIMS analysis shows that the crude product contains 96.1% of pure substance.

$^1$H No spectrum (CDCl$_3$/TMS):

δ=2.238 (3H); 3.677 (3H); 3.817 (2H); 5.307 (2H); 7.241–7.33 (3H); 7.42–7.49 (2H); 7.581/7.607 (1H); 7.798/7.824 (1H); 7.899 (1H) ppm.

GC/MS analysis:
  Retention index=2198
  M=366, 365, 346, 306, 198, 163, 145, 131, 105, 78, 39.

Step 6

(IX-1)

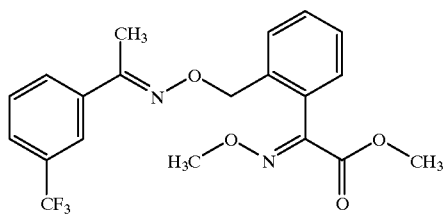

The preparation of this compound is described in Example 5 on page 11 of EP 600 835, starting from compound (X-1).

(Variant 2)

(II-1)

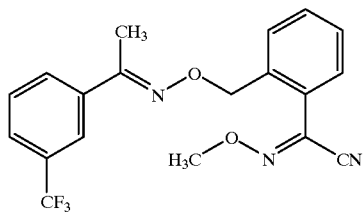

2.0 g (0.01 mol) of 3-trifluoromethylacetophenone oxime in 25 ml of dry dimethylformamide are first treated with 0.3 g (0.01 mol) of sodium hydride (80% in mineral oil) in portions with vigorous stirring and then -with 2.5 g (0.01 mol) of E-2-methoximino-2-(2-bromomethylphenyl)-acetonitrile.

The reaction mixture is stirred at 60° C. for 24 hours, subsequently cooled to room temperature, poured into water and extracted by shaking with ethyl acetate. The organic phase is washed with water, dried over sodium sulphate and concentrated in vacuo.

3.4 g (91% of theory) of E-2-methoximino-2-{2-[1-(3-trifluoromethylphenyl)-ethylideneiminooxymethyl]-phenyl}-acetonitrile are obtained as a yellow oil.

(XVII-1)

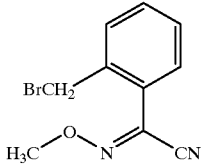

15.7 g (0.09 mol) of E-2-methoximino-2-(2-methylphenyl)-acetonitrile, 16.0 g (0.09 mol) of N-bromosuccinimide and 0.45 g of dibenzoyl peroxide are refluxed at the boil overnight in 130 ml of tetrachloromethane. The reaction mixture is then cooled to room temperature and filtered. The mother liquor is concentrated in vacuo and the residue chromatographed over silica gel (eluent: hexane/acetone 10:1).

10.0 g (44% of theory) of E-2-methoximino-2-(2-bromomethylphenyl)-acetonitrile are obtained as a highly viscous oil which is crystallized using petroleum ether; melting point=78–79° C.

(XXI-1)

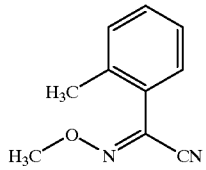

138.6 g (0.66 mol) of trifluoroacetic anhydride are added dropwise at 0° C. to a mixture of 77.2 g (0.4 mol) of E-2-methoxyimino-2-(2-methylphenyl)acetamide and 171.7 g of pyridine.

The reaction mixture is stirred at 0° C. for 1 hour, allowed to come to room temperature and subsequently stirred with 650 ml of concentrated hydrochloric acid. The mixture is then extracted by shaking with ethyl acetate, and the organic phase is washed with water, dried over sodium sulphate and concentrated in vacuo.

69.7 g (100% of theory) of E-2-methoximino-2-(2-methylphenyl)-acetonitrile are obtained.

$^1$H NMR (CDCl$_3$):d=2.3 (s, 3H).

(XX-1)

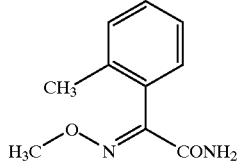

1.5 l of 25% strength ammonia water are added to 120 g (0.5 mol) of methyl E-2-methoximino-2-(2-methylphenyl)-acetate in 1.5 l of methanol and the mixture is refluxed for 5 hours. The reaction mixture is then allowed to cool, concentrated to approximately 1l, stirred with water and extracted by shaking with ethyl acetate. The organic phase is washed with water, dried over sodium sulphate and concentrated in vacuo. The residue is stirred with diisopropyl ether, filtered off with suction and dried.

66.2 g (69% of theory) of E-2-methoximino-2-(2-methylphenyl)-acetamide of melting point 98–99° C. are obtained.

Example 2

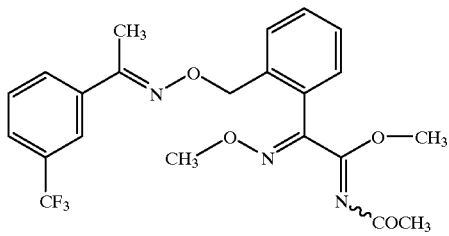

(Process b)

3.5 g (0.085 mol) of methyl E-2-methoximino-2-{2-[1-(3-trifluoromethylphenyl)-ethylideneimino oxymethyl]-phenyl}-acetimidate (Example 1) are dissolved in 30 ml of pyridine, 0.8 g (0.0102 mol) of acetyl chloride are added, and the mixture is stirred at room temperature overnight. The reaction mixture is concentrated, the residue is poured into water, the mixture is extracted using dichloromethane, and the dichloromethane phase is dried over sodium sulphate and reconcentrated. 3.6 g of a yellow oil of a methyl N-acetyl-2-(E-methoximino)-2-{2-[1-(3-trifluoromethylphenyl)ethylideneimino-oxymethyl]-phenyl}-acetimidate content of 76% (HPLC) are obtained as a stereoisomer mixture (ratio approximately 1:7, not assigned).

$^1$H NMR (CDCl$_3$): d=2.21; 2.26; 3.68; 3.97; 5.15; 7.15–7.95.

Example 3

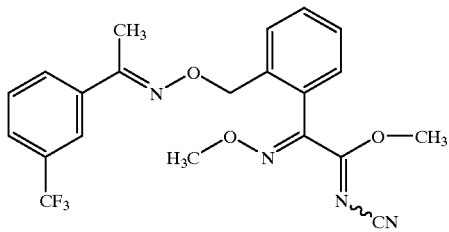

(Process c)

A solution of 3.6 g (0.01 mol) of disodium hydrogen phosphate and 1.6 g (0.01 mol) of sodium dihydrogen phosphate in 10 ml of water is added to 2.0 g (0.005 mol) of methyl E-2-methoximino-2-{2-[1-(3-trifluoromethylphenyl)-ethylideneiminooxymethyl]-phenyl}-acetimidate (Example 1) and 0.2 g (0.005 mol) of cyanamide, then 10 ml of methanol are added, and the mixture is stirred overnight at room temperature. The mixture is extracted with ether, and the ether phase is dried over sodium sulphate and concentrated.

The residue is chromatographed on silica gel using cyclohexane/ethyl acetate (3:1). 0.6 g (28%) of methyl N—cyano-2-(E-methoximino)-2-{2-[1-(3-trifluoromethylphenyl)-ethylideneiminooxymethyl]-phenyl}-acetimidate of melting point 93° C. are obtained.

Example 4

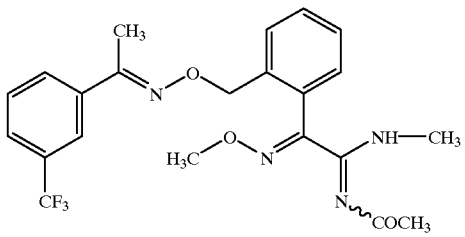

(Process d)

A solution of 0.08 g (0.0025 mol) of methylamine in 30 ml of tetrahydrofuran is added to a solution of 1.1 g (0.0025 mol) of methyl N-acetyl-2-(E-methoximino)- 2-{2-[1-(3-trifluoromethylphenyl)-ethylideneiminooxymethyl]-phenyl}-acetimidate (Example 2) in 30 ml of methanol, with ice-cooling. Stirring is continued at 20° C. for 18 hours. The solution is concentrated, and the residue is chromatographed on silica gel using cyclohexane/ethyl acetate (3:1). 0.44 g (39% of theory) of N-acetyl-2-(E-methoximino)-2-{2-[1-(3-trifluoromethylphenyl)-ethylideneiminooxy-methyl]-phenyl}-acetamidine is obtained.

Example 5

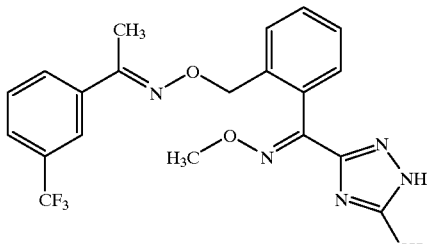

(Process e)

0.08 g (0.0025 mol) of hydrazine is added to a solution of 1.1 g (0.0025 mol) of methyl N-acetyl-2-(E-methoximino)-2-{2-[1-(3-trifluoromethylphenyl)-ethylideneiminooxymethyl]-phenyl}-acetimiidate (Example 2) in 30 ml of methanol, with ice-cooling. Stirring is continued at 20° C. for a further 18 hours. The solution is concentrated and the residue chromatographed on silica gel using cyclohexane/ethyl acetate (3:1). 0.42 g (39% of theory) of 5-methyl-3-[E-methoximino-2- {2-[1-(3-trifluoromethylphenyl)-ethylidene-iminooxymethyl]-phenyl}-triazole is obtained.

Example 6

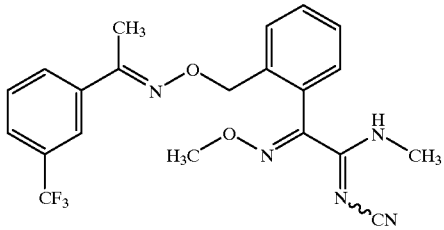

(Process d)

1 g (0.032 mol) of methylamine is passed into a solution of 1.4 g (0.0032 mol) of methyl N-cyano-2-(E-methoximino)-2-{2-[1-(3-trifluoromethylphenyl)ethylideneimino-oxymethyl]-phenyl}-acetimidate (Example 3) in 5 ml of methanol, with ice cooling. Stirring is continued at 20° C. for a further 18 hours. The solution is concentrated and the residue chromatographed on silica gel using cyclohexane/ethyl acetate (3:1). 0.42 g (31% of theory) of N-cyano-N'-methyl-2-(E-methoximino)-2-{2-[1-(3-trifluoromethylphenyl)-ethylidene-iminooxymethyl]-phenyl}-acetamidine is obtained.

$^1$H NMR (CDCl$_3$): δ=2.25; 4.05; 5.11 ppm.

Example 7

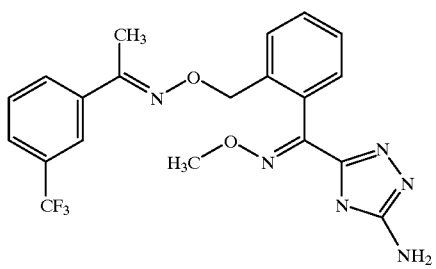

(Process e)

0.1 g (0.0032 mol) of hydrazine is added to a solution of 1.4 g (0.0032 mol) of methyl N-cyano-2-(E-methoximino)-2-{2-[1-(3-trifluoromethylphenyl)ethylidene-iminooxymethyl]-phenyl}-acetimidate (Example 3) in 10 ml of methanol, with ice-cooling. Stirring is continued at 20° C. for a further 18 hours. The solution is concentrated and the residue chromatographed on silica gel using cyclohexane/ethyl acetate (3:1). 0.46 g (33% of theory) of 5-amino-3-[E-methoximino-2-{2-[1-(3-trifluoromethylphenyl)-ethylideneiminooxymethyl]-phenyl}-triazole is obtained.

Example 8

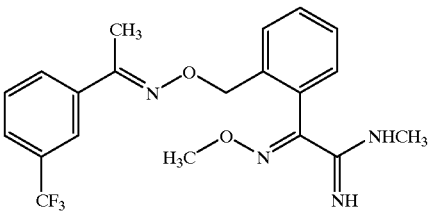

(Process f)

2.4 g (0.006 mol) of methyl E-2-methoximnino-2-{2-[1-(3-trifluoromethylphenyl)-ethylideneiminooxymethyl]-phenyl}-acetimidate (Example 1) are heated at boiling for 24 hours in 40 ml of a 30% strength solution of methylamine in ethanol. The reaction mixture is then concentrated in vacuo. 2.5 g (100% of theory) of N-methyl E-2-methoximino-2-{2-[1-(3-trifluoromethylphenyl)-ethylideneiminooxy-methyl]-phenyl}-acetimidamide are obtained as an oil.

$^1$H NMR (CDCl$_3$): d=2.95 (s, 3H).

The compounds of the general formula (I) listed in the table below are obtained analogously to Preparation Examples 1 to 8 and in accordance with the general description of the processes according to the invention:

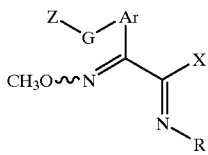

| Example No. | Z | G | Ar | R | X | Physical Data |
|---|---|---|---|---|---|---|
| 9 | 3,5-dimethylphenyl | C(CH$_3$)=N-O-CH$_2$- | 2-methylphenyl | H | OCH$_3$ | |
| 10 | 3-chlorophenyl | C(CH$_3$)=N-O-CH$_2$- | 2-methylphenyl | H | OCH$_3$ | |
| 11 | 3,4-dimethylphenyl | C(CH$_3$)=N-O-CH$_2$- | 2-methylphenyl | H | OCH$_3$ | |

-continued

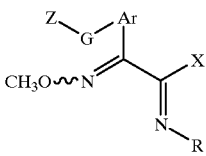

| Example No. | Z | G | Ar | R | X | Physical Data |
|---|---|---|---|---|---|---|
| 12 | 3,4-diCl-phenyl | C(CH₃)=N-O-CH₂CH₃ | 2-methylphenyl | H | OCH₃ | |
| 13 | 4-CH₃-phenyl | C(CH₃)=N-O-CH₂CH₃ | 2-methylphenyl | H | OCH₃ | |
| 14 | 4-CF₃-phenyl | C(CH₃)=N-O-CH₂CH₃ | 2-methylphenyl | H | OCH₃ | |
| 15 | 3-CH₃-phenyl | C(CH₃)=N-O-CH₂CH₃ | 2-methylphenyl | COCH₃ | OCH₃ | |
| 16 | 3-Cl-phenyl | C(CH₃)=N-O-CH₂CH₃ | 2-methylphenyl | COCH₃ | OCH₃ | |
| 17 | 3,4-diCH₃-phenyl | C(CH₃)=N-O-CH₂CH₃ | 2-methylphenyl | COCH₃ | OCH₃ | |
| 18 | 3,4-diCl-phenyl | C(CH₃)=N-O-CH₂CH₃ | 2-methylphenyl | COCH₃ | OCH₃ | |
| 19 | 4-CH₃-phenyl | C(CH₃)=N-O-CH₂CH₃ | 2-methylphenyl | COCH₃ | OCH₃ | |

-continued

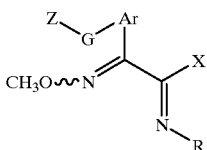

| Example No. | Z | G | Ar | R | X | Physical Data |
|---|---|---|---|---|---|---|
| 20 | 4-F₃C-C₆H₄ | C(CH₃)=N-O-Et | 2-methylphenyl | COCH₃ | OCH₃ | |
| 21 | 2-methylphenyl | C(CH₃)=N-O-Et | 2-methylphenyl | CN | OCH₃ | |
| 22 | 3-Cl-C₆H₄ | C(CH₃)=N-O-Et | 2-methylphenyl | CN | OCH₃ | |
| 23 | 3,4-(CH₃)₂-C₆H₃ | C(CH₃)=N-O-Et | 2-methylphenyl | CN | OCH₃ | |
| 24 | 3,4-Cl₂-C₆H₃ | C(CH₃)=N-O-Et | 2-methylphenyl | CN | OCH₃ | ¹H-NMR (CDCl₃): δ = 2.21; 3.69; 4.11; 4.61 |
| 25 | 4-CH₃-C₆H₄ | C(CH₃)=N-O-Et | 2-methylphenyl | CN | OCH₃ | |
| 26 | 4-F₃C-C₆H₄ | C(CH₃)=N-O-Et | 2-methylphenyl | CN | OCH₃ | |
| 27 | 3-CF₃-C₆H₄ | C(CH₃)=N-O-Et | 2-methylphenyl | H | NH₂ | |

-continued

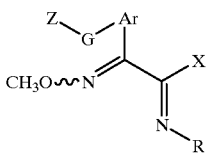

| Example No. | Z | G | Ar | R | X | Physical Data |
|---|---|---|---|---|---|---|
| 28 | 3,5-dimethylphenyl | C(CH₃)=N-O-ethyl | 2-methylphenyl | H | NH₂ | |
| 29 | 3-chlorophenyl | C(CH₃)=N-O-ethyl | 2-methylphenyl | H | NH₂ | |
| 30 | 2,4-dimethylphenyl | C(CH₃)=N-O-ethyl | 2-methylphenyl | H | NH₂ | |
| 31 | 3,4-dichlorophenyl | C(CH₃)=N-O-ethyl | 2-methylphenyl | H | NH₂ | |
| 32 | 4-(trifluoromethyl)phenyl | C(CH₃)=N-O-ethyl | 2-methylphenyl | H | NH₂ | |
| 33 | 4-methylphenyl | C(CH₃)=N-O-ethyl | 2-methylphenyl | H | NH₂ | |
| 34 | 3,5-dimethylphenyl | C(CH₃)=N-O-ethyl | 2-methylphenyl | H | NHCH₃ | |
| 35 | 3-chlorophenyl | C(CH₃)=N-O-ethyl | 2-methylphenyl | H | NHCH₃ | |

-continued

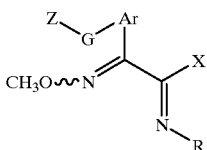

| Example No. | Z | G | Ar | R | X | Physical Data |
|---|---|---|---|---|---|---|
| 36 | 2,4-dimethylphenyl | C(CH₃)=N-O-C₂H₅ | 2-methylphenyl | H | NHCH₃ | |
| 37 | 2,4-dichlorophenyl | C(CH₃)=N-O-C₂H₅ | 2-methylphenyl | H | NHCH₃ | |
| 38 | 4-(trifluoromethyl)phenyl | C(CH₃)=N-O-C₂H₅ | 2-methylphenyl | H | NHCH₃ | |
| 39 | 4-methylphenyl | C(CH₃)=N-O-C₂H₅ | 2-methylphenyl | H | NHCH₃ | |
| 40 | 3-(trifluoromethyl)phenyl | C(CH₃)=N-O-C₂H₅ | 2-methylphenyl | H | NHC₂H₅ | 1H-NMR (CDCl₃) δ (ppm) = 2.25 (s, 3H) |
| 41 | 3-methylphenyl | C(CH₃)=N-O-C₂H₅ | 2-methylphenyl | H | NHC₂H₅ | |
| 42 | 3-chlorophenyl | C(CH₃)=N-O-C₂H₅ | 2-methylphenyl | H | NHC₂H₅ | |
| 43 | 2,4-dimethylphenyl | C(CH₃)=N-O-C₂H₅ | 2-methylphenyl | H | NHC₂H₅ | |

-continued

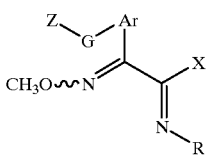

| Example No. | Z | G | Ar | R | X | Physical Data |
|---|---|---|---|---|---|---|
| 44 | 3,4-diCl-phenyl | C(CH₃)=N-OC₂H₅ | 2-methylphenyl | H | NHC₂H₅ | |
| 45 | 4-CF₃-phenyl | C(CH₃)=N-OC₂H₅ | 2-methylphenyl | H | NHC₂H₅ | |
| 46 | 4-CH₃-phenyl | C(CH₃)=N-OC₂H₅ | 2-methylphenyl | H | NHC₂H₅ | |
| 47 | 3-CF₃-phenyl | C(CH₃)=N-OC₂H₅ | 2-methylphenyl | COCH₃ | NH₂ | |
| 48 | 3-CH₃-phenyl | C(CH₃)=N-OC₂H₅ | 2-methylphenyl | COCH₃ | NH₂ | |
| 49 | 3-Cl-phenyl | C(CH₃)=N-OC₂H₅ | 2-methylphenyl | COCH₃ | NH₂ | |
| 50 | 3,4-diCH₃-phenyl | C(CH₃)=N-OC₂H₅ | 2-methylphenyl | COCH₃ | NH₂ | |
| 51 | 3,4-diCl-phenyl | C(CH₃)=N-OC₂H₅ | 2-methylphenyl | COCH₃ | NH₂ | |

-continued

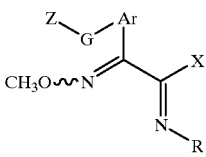

| Example No. | Z | G | Ar | R | X | Physical Data |
|---|---|---|---|---|---|---|
| 52 | 4-CF₃-C₆H₄ | C(CH₃)=NOC₂H₅ | 2-CH₃-C₆H₄ | COCH₃ | NH₂ | |
| 53 | 4-CH₃-C₆H₄ | C(CH₃)=NOC₂H₅ | 2-CH₃-C₆H₄ | COCH₃ | NH₂ | |
| 54 | 3-CF₃-C₆H₄ | C(CH₃)=NOC₂H₅ | 2-CH₃-C₆H₄ | COCH₃ | NHCH₃ | |
| 55 | 3-CH₃-C₆H₄ | C(CH₃)=NOC₂H₅ | 2-CH₃-C₆H₄ | COCH₃ | NHCH₃ | |
| 56 | 3-Cl-C₆H₄ | C(CH₃)=NOC₂H₅ | 2-CH₃-C₆H₄ | COCH₃ | NHCH₃ | |
| 57 | 3,4-(CH₃)₂-C₆H₃ | C(CH₃)=NOC₂H₅ | 2-CH₃-C₆H₄ | COCH₃ | NHCH₃ | |
| 58 | 3,4-Cl₂-C₆H₃ | C(CH₃)=NOC₂H₅ | 2-CH₃-C₆H₄ | COCH₃ | NHCH₃ | |
| 59 | 4-CF₃-C₆H₄ | C(CH₃)=NOC₂H₅ | 2-CH₃-C₆H₄ | COCH₃ | NHCH₃ | |

-continued

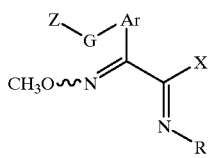

| Example No. | Z | G | Ar | R | X | Physical Data |
|---|---|---|---|---|---|---|
| 60 | 4-CH₃-C₆H₄- | C(CH₃)=NOC₂H₅ | 2-CH₃-C₆H₄- | COCH₃ | NHCH₃ | |
| 61 | 3-CF₃-C₆H₄- | C(CH₃)=NOC₂H₅ | 2-CH₃-C₆H₄- | COCH₃ | NHC₂H₅ | |
| 62 | 3-CH₃-C₆H₄- | C(CH₃)=NOC₂H₅ | 2-CH₃-C₆H₄- | COCH₃ | NHC₂H₅ | |
| 63 | 2-CH₃-C₆H₄- | C(CH₃)=NOC₂H₅ | 2-CH₃-C₆H₄- | COCH₃ | NH₂ | ¹H-NMR (CDCl₃) δ (ppm) = 3.95 (s, 3H) |
| 64 | 3-CF₃-C₆H₄- | C(CH₃)=NOC₂H₅ | 2-methyl-thien-3-yl | H | OCH₃ | ¹H-NMR (CDCl₃) δ (ppm) = 2.3 (s, 3H) |
| 65 | 3-CF₃-C₆H₄- | C(CH₃)=NOC₂H₅ | 2-methyl-thien-3-yl | COCH₃ | OCH₃ | ¹H-NMR (CDCl₃) δ (ppm) = 2.3 (s, 3H) |
| 66 | 3-CF₃-C₆H₄- | C(CH₃)=NOC₂H₅ | 2-methyl-thien-3-yl | H | OC₂H₅ | NMR: δ = 2.3 (s, 3H) |
| 67 | 3-CF₃-C₆H₄- | C(CH₃)=NOC₂H₅ | 2-methyl-thien-3-yl | H | NHC₂H₅ | NMR: δ = 2.25 (s, 3H) |

-continued

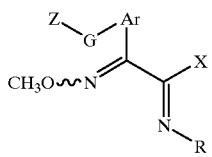

| Example No. | Z | G | Ar | R | X | Physical Data |
|---|---|---|---|---|---|---|
| 68 | 3-CF₃-phenyl- | -C(CH₃)=N-O-CH₂CH₃ | 2-methylphenyl | CONHCH₃ | OCH₃ | NMR: δ = 5.15 (s, 2H) |
| 69 | 3-CF₃-phenyl- | -C(CH₃)=N-O-CH₂CH₃ | 2-methylphenyl | CH₃ | N(CH₃)—CO—NH—CH₃ | NMR: δ = 5.2 (s, 2H) |
| 70 | H₃C— | — | 2-methylphenyl | H | OCH₃ | ¹H-NMR: δ = 2.17 (s, 3H); 3.89 (s, 3H); 3.99 (s, 3H) |
| 71 | H₃C— | — | 2-methylphenyl | CN | OCH₃ | Fp.: 158° C. |
| 72 | Br—CH₂— | — | 2-methylphenyl | CN | OCH₃ | Fp.: 103° C. |
| 73 | 3-CF₃-phenyl- | -C(CH₃)=N-O-CH₂CH₃ | 2-methylphenyl | CH₃SO₂ | NHCH₃ | ¹H-NMR (CDCl₃); δ = 3.1 (s, 3H) |
| 74 | 3-CF₃-phenyl- | -C(CH₃)=N-O-CH₂CH₃ | 2-methylphenyl | CF₃SO₂ | NHCH₃ | ¹H-NMR (CDCl₃); δ = 4.05 (s, 3H) |
| 75 | 3-CF₃-phenyl- | -C(CH₃)=N-O-CH₂CH₃ | 2-methylphenyl | CH₃O—CO | NHCH₃ | ¹H-NMR (CDCl₃); δ = 3.95 (s, 3H) |

-continued

| Example No. | Z | G | Ar | R | X | Physical Data |
|---|---|---|---|---|---|---|
| 76 | H3C-/CH3-aryl with N~OCH3 (3,4-dimethylphenyl with C(=NOCH3)) | —O—CH2— | o-tolyl | —COCH3 | —OCH3 | $^1$H-NMR (CDCl$_3$); δ = 4,0 |
| 77 | H3C-/CH3-aryl with N~OCH3 (3,4-dimethylphenyl with C(=NOCH3)) | —O—CH2— | o-tolyl | —CN | —OCH3 | $^1$H-NMR (CDCl$_3$); δ = 4,0 |

APPLICATION EXAMPLES

Example A
Podosphaera test (apple)/protective
Solvent: 4.7 parts by weight of acetone
Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the causative organism of apple mildew (*Podosphaera leucotricha*).

The plants are then placed in a greenhouse at 23° C. and a relative atmospheric humidity of about 70%.

Evaluation is carried out 10 days after the inoculation.

In this test, a degree of effectiveness of up to 100% is shown by the compound of Preparation Example 1 at a concentration of active compound of 20 ppm.

Example B
Venturia test (apple)/protective
Solvent: 4.7 parts by weight of acetone
Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, an outstanding degree of effectiveness is shown by the compound of Preparation Example 1.

Example C
Erysiphe test (barley)/protective
Solvent: 10 parts by weight of N-methyl-pyrrolidone
Emulsifier: 0.6 part by weight of allyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate shown. After the spray coating has dried on, the plants are dusted with spores of *Erysiphe graminis* f.sp. *hordei*.

The plants are then placed in a greenhouse at a temperature of about 20° C. and a relative atmospheric humidity of about 80%, in order to promote the development of powdery mildew pustules.

Evaluation is carried out 7 days after the inoculation.

In this test, a degree of effectiveness of 100% is shown by the compound of Preparation Example 1 at a rate of active compound of 250 g/ha.

Example D
Erysiphe test (barley)/curative
Solvent: 10 parts by weight of N-methyl-pyrrolidone
Emulsifier: 0.6 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis* f. sp. *hordei*. 48 hours after the inoculation, the plants are sprayed with the preparation of active compound at the application rate shown.

The plants are then placed in a greenhouse at a temperature of about 20° C. and a relative atmospheric humidity of about 80%, in order to promote the development of powdery mildew pustules.

Evaluation is carried out 7 days after the inoculation.

In this test, a degree of effectiveness of 100% is shown by the compound of Preparation Example 1 at a rate of active compound of 250 g/ha.

Example E
Erysiphe test (wheat)/protective
Solvent: 10 parts by weight of N-methyl-pyrrolidone
Emulsifier: 0.6 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate shown. After the spray coating has dried on, the plants are dusted with spores of Erysiphe graminis f.sp. tritici.

The plants are then placed in a greenhouse at a temperature of about 20° C. and a relative atmospheric humidity of about 80%, in order to promote the development of powdery mildew pustules.

Evaluation is carried out 7 days after the inoculation.

In this test, a degree of effectiveness of 100% is shown by the compound of Preparation Example I at a rate of active compound of 250 g/ha.

Example F
Erysiphe test (wheat)/curative
Solvent: 10 parts by weight of N-methyl-pyrrolidone
Emulsifier: 0.6 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f. sp. tritici. 48 hours after the inoculation, the plants are sprayed with the preparation of active compound at the application rate shown.

The plants are then placed in a greenhouse at a temperature of about 20° C. and a relative atmospheric humidity of about 80%, in order to promote the development of powdery mildew pustules.

Evaluation is carried out 7 days after the inoculation.

In this test, a degree of effectiveness of 100% is shown by the compound of Preparation Example 1 at a rate of active compound of 250 g/ha.

What is claimed is:

1. An imidic acid derivative of the formula (I)

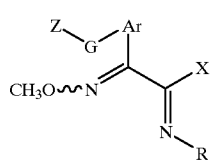

(I)

in which
R represents cyano,
X represents in each case straight-chain or branched alkoxy or alkylthio, each of which has 1 to 4 carbon atoms;
amino or in each case straight-chain or branched alkylamino and dialkylamino, each of which has 1 to 4 carbon atoms in the individual alkyl moieties,
Ar represents in each case optionally substituted phenylene or naphthylene, the substituents being selected from the group consisting of:
halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl, alkenyloxy or alkinyloxy, each of which has 2 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl moieties, and in each case divalent alkylene or dioxyalkylene, each of which has 1 to 6 carbon atoms and each of which is optionally monosubstituted or potysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms,
G represents a single bond, represents oxygen, or represents in each case optionally halogen-, hydroxyl-, $C_1$–$C_4$-alkyl-, $C_1$–$C_4$-halogenoalkyl- or $C_3$–$C_6$-cycloalkyl-substituted alkanediyl, alkenediyl, oxaalkenediyl or alkinediyl, each of which has up to 4 carbon atoms, or one of the groups which follow:
-Q—CQ-, —CQ-Q-, —CH$_2$—Q-; -Q—CH$_2$—, —CQ-Q—CH$_2$—, —CH$_2$—Q—CQ-, -Q—CQ—CH$_2$—, -Q—CQ-Q—CH$_2$—, —N=N—, —S(O)$_n$—, —CH$_2$—S(O)$_n$—, —CQ-, —S(O)$_n$—CH$_2$—, —C(R$^4$)=N—O—, —C(R$^4$)=N—O—CH$_2$—, -Q—C(R$^4$)=N—O—CH$_2$—, —NH—C(R$^4$)=N—O—CH$_2$—, —N(R$^5$)-, —CQ—N(R$^5$)-, —N(R$^5$)—CQ-, -Q—CQ—N(R$^5$)-, —N=C(R$^4$)-Q—CH$_2$—, —CH$_2$—O—N=C(R$^4$)-, —N(R$^5$)—CQ-Q-, —CQ—N(R$^5$)—CQ-Q-, —N(R$^5$)—CQ-Q—CH$_2$—, —CQ—CH$_2$— or —N=N—C(R$^4$)=N—,
where
n represents the numbers 0, 1 or 2,
Q represents oxygen or sulphur,
R$^4$ represents hydrogen, cyano, or represents alkyl, alkoxy, alkylthio, alkylamino or dialkylamino, each of which has 1 to 6 carbon atoms in the alkyl groups and is optionally substituted by halogen, cyano or $C_1$–$C_4$-alkoxy, or represents cycloalkyl having 3 to 6 carbon atoms which is optionally substituted by halogen, cyano, carboxyl, $C_1$–$C_4$-alkyl or $C_1$–$C_4$-alkoxycarbonyl, and
R$^5$ represents hydrogen, hydroxyl, cyano, or represents alkyl having 1 to 6 carbon atoms which is optionally substituted by halogen, cyano or $C_1$–$C_4$-alkoxy, or represents cycloalkyl having 3 to 6 carbon atoms which is optionally substituted by halogen, cyano, carboxyl, $C_1$–$C_4$-alkyl or $C_1$–$C_4$-alkoxycarbonyl, Z represents allyl having 1 to 8 carbon atoms which is optionally substituted by halogen, cyano, hydroxyl, amino, $C_1$–$C_4$-alkoxy, $C_1$–$C_4$-alkylthio, $C_1$–$C_4$-alkylsulphinyl or $C_1$–$C_4$-alkylsulphonyl (which are in each case optionally substituted by halogen), or represents alkenyl or alkinyl; each of which has up to 8 carbon atoms and is optionally substituted by halogen, or represents cycloalkyl having 3 to 6 carbon atoms which is optionally substituted by halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl, or represents in each case optionally substituted phenyl, naphthyl the substituents being selected from the the group consisting of:

halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogeno alkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl moieties, in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, or cycloalkyl having 3 to 6 carbon atoms, or phenyl, phenoxy, benzyl, benzyloxy, phenylethyl or phenylethyloxy, each of which is optionally monosubstituted or polysubstituted in the phenyl moiety by identical or different substituents from the series consisting of halogen, cyano, nitro, carboxyl, carbamoyl and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkoxy having 1 to 4 carbon atoms and 1 to 9 identical or different halogen atoms and/or alkylcarbonyl or alkoxycarbonyl, each of which has up to 5 carbon atoms.

2. A compound of the formula (I) according to claim 1, in which

R represents cryano,

X represents methoxy, ethoxy, n- or i-propoxy, n-, i-, s- or t-butoxy; methylthio, ethylthio, n- or i-propylthio, n-, i-, s- or t-butylthio; amino, methylamino, ethylarino, n- or i-propylamino; dimethylamino, methylethyl-amino, diethylamino, methyl-n- or i-propylamino and ethyl-n- or i-propylamino;

Ar represents in each case optionally substituted ortho-, meta- or paraphenylene, the substituents being selected from the group consisting of:

fluorine, chlorine, cyano, methyl, ethyl, trifluoromethyl, methoxy, ethoxy, methylthio, methylsulphinyl or methylsulphonyl;

G represents a single bond, represents oxygen or represents in each case optionally fluorine-, chlorine-, hydroxyl-, methyl-, ethyl-, n- or i-propyl-, rifluoromethyl-, cyclopropyl-, cyclobutyl-, cyclopentyl- or cyclohexyl-substituted methylene, dimethylene (ethane-1,2-diyl), ethene-1,2-diyl, ethine-1,2-diyl or one of the groups which follow -Q—CQ-, —CQ-Q-, —CH$_2$—Q-; -Q—CH$_2$—, —CQ-Q—CH$_2$—, —CH$_2$—Q—CQ-, -Q—CQ—CH$_2$—, -Q—CQ-Q—CH$_2$—, —N═N—, —S(O)$_n$—, —CH$_2$—S(O)$_n$—, —CQ-, —S(O)$_n$—CH$_2$—, —C(R$^4$)═N—O—, —C(R$^4$)═N—0—CH$_2$—, -Q—C(R$^4$)═N—O—CH$_2$—, —NH—C(R$^4$)═N—O—CH$_2$—, —N(R$^5$)-, —CQ—N(R$^5$)-, —N(R$^5$)—CQ-, -Q—CQ-N(R$^5$)-, —N═C(R$^4$)-Q—CH$_2$—, —CH$_2$—O—N═C(R$^4$)-, —N(R$^5$)—CQ-Q-, —CQ—N(R$^5$)—CQ-Q- or —N(R$^5$)—CQ-Q—CH$_2$—, where n represents the numbers 0, 1 or 2, Q represents oxygen or sulphur, R$^4$ represents hydrogen, cyano, or represents methyl, ethyl, n- or i-propyl, n-, i- or s-butyl, methoxy, ethoxy, propoxy, butoxy, methylthio, ethylthio, propylthio, butylthio, methylarnino, ethylamino, propylamino, dimethylamino or diethylarnino, which is optionally substituted by fluorine, chlorine, cyano, methoxy or ethoxy, or represents cyclopropyl, cyclobutyl, cyclopentyl or cyclohexyl, each of which is optionally substituted by fluorine, chlorine, cyano, carboxyl, methyl, ethyl, n- or i-propyl, methoxycarbonyl or ethoxycarbonyl, and R$^5$ represents hydrogen, hydroxyl, cyano, or represents methyl, ethyl, n- or i-propyl or n-, i-, s- or t-butyl, each of which is optionally substituted by fluorine, chlorine, cyano, methoxy or ethoxy, or represents cyclopropyl, cyclobutyl, cyclopentyl or cyclohexyl, each of which is optionally substituted by fluorine, chlorine, cyano, carboxyl, methyl, ethyl, n- or i-propyl, methoxycarbonyl or ethoxycarbonyl;

Z represents methyl, ethyl, n- or i-propyl or n-, i-, s- or t-butyl, which is optionally substituted by fluorine, chlorine, bromine, cyano, hydroxyl, amino, methoxy, ethoxy, methylthio, ethylthio, methylsulphinyl, ethyl-sulphinyl, methylsulphonyl or ethylsulphonyl (which are in each case optionally substituted by fluorine and/or chlorine), or represents allyl, crotonyl, 1-methyl-allyl, propargyl or 1-methyl-propargyl, each of which is optionally substituted by fluorine, chlorine or bromine, or represents cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, — or i-propyl, methoxycarbonyl or ethoxycarbonyl, or represents in each case optionally substituted phenyl, naphthyl, the substituents being selected from the group consisting of:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl; trimethylene (propane-1,3-diyl), methylenedioxy or ethylenedioxy), cyclopropyl, cyclobutyl, cyclopentyl or cyclohexyl, each of which is optionally monosubstituted or polysubstituted by identical or different substituents from the series consisting of fluorine, chlorine, methyl, ethyl or n- or i-propyl, and phenyl, phenoxy, benzyl or benzyloxy, each of which is optionally monosubstituted or polysubstituted in the phenyl moiety by identical or different substituents from the series consisting of fluorine, chlorine, bromine, cyano, nitro, carboxyl, carbamoyl, methyl, ethyl, n- or i-propyl, n-, i-, s- or t-butyl, trifluoromethyl, methoxy, ethoxy, n- or i-propoxy, difluoromethoxy, trifluoromethoxy, acetyl, methoxycarbonyl or ethoxycarbonyl.

3. A compound of the formula (I) according to claim 1 in which

R represents cyano,

X represents methoxy, ethoxy, methylthio, ethylthio, amino, methylamino, ethylamino, dimethylamino or diethylamino;

Ar represents ortho-phenylene;

G represents oxygen, methylene or one of the groups which follow

—CH$_2$—O—, —O—CH$_2$—, —S(O)$_n$—, —CH$_2$—S(O)$_n$—, —S(O)$_n$—CH$_2$—, —C(R$^4$)=N—O—, —O—N=C(R$^4$)-, —C(R$^4$)=N—O—CH$_2$—, —O—C(R$^4$)=N—O—CH$_2$—, —NH—CR($^4$)=—N—O—CH$_2$—, —N(R$^5$)- or —CH$_2$—O—N=C(R$^4$)-, where n represents the numbers 0, 1 or 2, R$^4$ represents hydrogen, methyl or ethyl and R$^5$ represents hydrogen, methyl or ethyl;

Z represents in each case optionally substituted phenyl, the substituents being selected from the group consisting of:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, methylenedioxy or ethylenedioxy, each of which is optionally monosubstituted or polysubstituted by identical or different substituents from the series consisting of fluorine, chlorine, methyl or ethyl, or phenyl, phenoxy, benzyl or benzyloxy, each of which is optionally monosubstituted or polysubstituted in the phenyl moiety by identical or different substituents from the series consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

4. Compounds of the formula (I) according to claim 1 in which

Ar represents ortho-phenylene.

5. Process for the preparation of compounds of the formula (I) according to claim 1, characterized in that a) nitriles of the general formula (II)

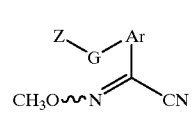

(II)

in which

Ar, G and Z have the meanings given in claim 1 are reacted with (thio)alcohols of the general formula (III)

 (III)

in which

X$^1$ represents alkoxy or alkylthio, or with their alkali metal salts, if appropriate in the presence of a diluent and if appropriate in the presence of a reaction auxiliary;

or b) the imidates which can be obtained by process (a) which have the general formula (Ia)

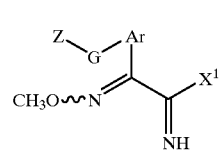

(Ia)

in which

Ar, G, Z and X$^1$ have the abovementioned meanings, are reacted with reactive acid derivatives, in particular with acid halides of the general formula (IV)

 (IV)

in which

R has the meaning in claim 1 and

Hal represents halogen, or with the corresponding anhydrides, if appropriate in the presence of a diluent and if appropriate in the presence of a reaction auxiliary;

or c) the imidates which can be obtained by process (a) which have the general formula (Ia)

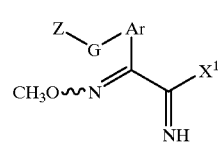

(Ia)

in which

Ar, G, Z and X$^1$ have the abovementioned meanings, are reacted with cyanamide, of the formula (V), $$NH_2-CN \quad (V)$$

if appropriate in the presence of a diluent and if appropriate in the presence of a reaction auxiliary;
or d) the imidic acid derivatives which can be obtained by processes (b) and (c) which have the general formula (Ib)

(Ib)

[Structure: Z-G(Ar)=C(X¹)-N=N-R' with CH₃O~~N]

in which
  Ar, G, Z and X¹ have the abovementioned meanings and
  R' represents cyano
  are reacted with amines of the general formula (VI)

$$H-X^2 \quad (VI)$$

in which
  X² represents amino, alkylamino or dialkylamino,
  if appropriate in the presence of a diluent;
or e) the imidic acid derivatives which can be obtained by processes (b) and (c) which have the general formula (Ic)

(Ic)

[Structure: Z-G(Ar)=C(OCH₃)-N=N-R' with CH₃O~~N]

in which
  Ar, G, Z and R' have the abovementioned meanings, are reacted with hydrazine or hydrazine hydrate, if appropriate in the presence of a diluent;
or f) the imidates which can be obtained by process (a) which have the general formula (Ia)

(Ia)

[Structure: Z-G(Ar)=C(X¹)-NH with CH₃O~~N]

in which
  Ar, G, Z and X¹ have the abovementioned meanings,
  are reacted with amines of the general formula (VI)

$$H-X^2 \quad (VI)$$

in which
  X² has the abovementioned meaning,
  if appropriate in the presence of a diluent.

6. A pesticidal composition comprising a pesticidally effective amount of a compound according to claim 1 and a diluent.

7. A method of combating unwanted pests which comprises administering to such pests or to a locus from which it is desired to exclude such pests a pesticidally effective amount of a compound according to claim 1.

8. An imidic acid derivative of the formula

[Structure: 3-CF₃-phenyl-C(CH₃)=N-O-CH₂-(o-phenyl)-C(OCH₃)=N-N=CN with H₃C-O-N]

* * * * *